US006969769B2

(12) United States Patent
Worley et al.

(10) Patent No.: US 6,969,769 B2
(45) Date of Patent: Nov. 29, 2005

(54) N-HALAMINE SILOXANES FOR USE IN BIOCIDAL COATINGS AND MATERIALS

(75) Inventors: Shelby D. Worley, Auburn, AL (US); Yongjun Chen, Auburn, AL (US); Jia-Wang Wang, Auburn, AL (US); Rong Wu, Auburn, AL (US); Yanjun Li, Kirkland, WA (US)

(73) Assignee: Vanson Halosource, Inc., Redmond, WA (US)

( * ) Notice: Subject to any disclaimer, the term of this patent is extended or adjusted under 35 U.S.C. 154(b) by 0 days.

(21) Appl. No.: 10/400,165

(22) Filed: Mar. 24, 2003

(65) Prior Publication Data

US 2004/0127667 A1 Jul. 1, 2004

Related U.S. Application Data

(60) Provisional application No. 60/388,968, filed on Jun. 14, 2002.

(51) Int. Cl.[7] .............................................. C08G 77/24
(52) U.S. Cl. ...................... 548/110; 556/425; 556/413; 528/28; 528/38; 428/447
(58) Field of Search ................................ 556/425, 413; 548/110; 528/28, 38; 428/447

(56) References Cited

U.S. PATENT DOCUMENTS

| | | | |
|---|---|---|---|
| 2,950,553 A | 8/1960 | Hurwitz | |
| 3,519,608 A | 7/1970 | Kelley | |
| 3,547,943 A | 12/1970 | Senge et al. | |
| 3,560,385 A | 2/1971 | Roth | |
| 3,730,701 A | 5/1973 | Isquith et al. | |
| 3,779,991 A | 12/1973 | Preston | |
| 3,794,736 A | 2/1974 | Abbott et al. | |
| 3,812,201 A | 5/1974 | Bey | |
| 3,814,739 A | 6/1974 | Takeda | |
| 3,821,218 A | 6/1974 | Berger | |
| 3,860,709 A | 1/1975 | Abbott et al. | |
| 3,931,213 A | 1/1976 | Kaminski et al. | |
| 4,000,293 A | 12/1976 | Kaminski et al. | |
| 4,075,167 A * | 2/1978 | Takamizawa et al. | ......... 528/32 |
| 4,082,635 A | 4/1978 | Fritz et al. | |
| 4,282,366 A | 8/1981 | Eudy | |
| 4,408,996 A | 10/1983 | Baldwin | |
| 4,411,928 A | 10/1983 | Baldwin | |
| 4,412,078 A * | 10/1983 | Berger | ......................... 548/110 |
| 4,414,268 A | 11/1983 | Baldwin | |
| 4,417,066 A | 11/1983 | Westall | |
| 4,448,969 A | 5/1984 | Ramey et al. | |
| 4,504,541 A | 3/1985 | Yasuda et al. | |
| 4,560,766 A | 12/1985 | Girard et al. | |
| 4,615,937 A | 10/1986 | Bouchette | |
| 4,654,424 A | 3/1987 | Girard et al. | |
| 4,681,948 A | 7/1987 | Worley | |
| 4,684,726 A | 8/1987 | Greco et al. | |
| 4,692,374 A | 9/1987 | Bouchette | |
| 4,729,986 A | 3/1988 | Olson | |
| 4,767,542 A | 8/1988 | Worley | |
| 5,057,612 A | 10/1991 | Worley et al. | |
| 5,126,057 A | 6/1992 | Worley et al. | |
| 5,194,504 A | 3/1993 | Lebovits et al. | |
| 5,490,983 A | 2/1996 | Worley et al. | |
| 5,756,751 A * | 5/1998 | Schmalstieg et al. | ....... 548/110 |
| 5,756,764 A | 5/1998 | Fenteany et al. | |
| 5,882,357 A | 3/1999 | Sun et al. | |
| 5,902,818 A | 5/1999 | Worley et al. | |
| 5,954,869 A | 9/1999 | Elfersy et al. | |
| 6,106,653 A * | 8/2000 | Polizzotti et al. | ......... 156/272.2 |
| 6,294,185 B1 | 9/2001 | Worley et al. | |
| 6,297,383 B1 * | 10/2001 | Berger et al. | ............... 548/110 |
| 6,469,177 B1 | 10/2002 | Worley et al. | |
| 6,548,054 B2 | 4/2003 | Worley et al. | |
| 2003/0064645 A1 | 4/2003 | Worley et al. | |

FOREIGN PATENT DOCUMENTS

| | | |
|---|---|---|
| GB | 2 137 217 A | 10/1984 |
| WO | WO 89/10696 A | 11/1989 |
| WO | 03/106466 | * 12/2003 |

OTHER PUBLICATIONS

Michael Roth, "Siliconates—Silicon resins—Silanes—Siloxanes", Feb. 1982.*
Li, Y., and S.D. Worley, "Biocidal Copolymers of N–Haloacryloxymethylhydantion," *Journal of Bioactive and Compatible Polymers* 16:493–506, 2001.
Sugama, T, and J.E. DuVall, "Polyorganosiloxane–Grafted Potato Starch Coatings for Protecting Aluminum From Corrosion," *Thin Solid Films* 289:39–48, 1995.
Anderson, R., et al., "Silicon Compounds Register and Review," Petrarch Systems, 1987, 1 pg.
Borman, S., "Designed Surface Kills Bacteria, Polymer Coated on Glass Surface Zaps Airborne Microbes on Contact," *C&EN*, May 28, 2001, p. 13.
Hazziza–Laskar, J., et al., "Biocidal Polymers Active by Contact. IV. Polyurethanes Based on Polysiloxanes with Pendant Primary Alcohols and Quaternary Ammonium Groups," *Journal of Applied Polymer Science* 58:77–84, 1995.

(Continued)

*Primary Examiner*—Margaret G. Moore
(74) *Attorney, Agent, or Firm*—Christensen O'Connor Johnson Kindness PLLC

(57) ABSTRACT

Heterocyclic and acyclic silane monomers and siloxane polymers, and their halogenated derivatives, are provided for the purpose of functionalizing surfaces or materials so as to render them biocidal upon exposure to oxidative halogen solutions. The biocidal function can be imparted either before or after bonding or adhesion to the surface or material. The biocidal surfaces and materials can then be used to inactivate pathogenic microorganisms such as bacteria, fungi, and yeasts, as well as virus particles, which can cause infectious diseases, and those microorganisms which cause noxious odors and unpleasant coloring such as mildew. Examples of surfaces and materials which can be rendered biocidal in this invention include, but are not limited to, cellulose, chitin, chitosan, synthetic fibers, glass, ceramics, plastics, rubber, cement grout, latex caulk, porcelain, acrylic films, vinyl, polyurethanes, silicon tubing, marble, metals, metal oxides, and silica.

125 Claims, 1 Drawing Sheet

OTHER PUBLICATIONS

Kanazawa, A., et al., "Polymeric Phosphonium Salts as a Novel Class of Cationic Biocides. VI. Antibacterial Activity of Fibers Surface–Treated with Phosphonium Salts Containing Trimethoxysilane Groups," *Journal of Applied Polymer Science* 52:641–647, 1994.

Mintz, M.J., and C. Walling, "t–Butyl Hypochlorite," *Org. Syn.*, 5:1–3, 1969. <http://www.orgsyn.org/orgsyn/prepcontent.asp?print=1&prep=cv . . . > [retrieved Jun. 27, 2003], pp. 1–3.

Nurdin, N., et al., "Biocidal Polymers Active by Contact. II. Biological Evaluation of Polyurethane Coatings with Pendant Quaternary Ammonium Salts," *Journal of Applied Polymer Science* 50(4):663–670, 1993.

Nurdin, N., et al., "Biocidal Polymers Active by Contact. III. Ageing of Biocidal Polyurethane Coatings in Water," *Journal of Applied Polymer Science* 50(4):671–678, 1993.

Panangala, V.S., et al., Inactivation of Rotavirus by New Polymeric Water Disinfectants, *Journal of Virological Methods* 66:263–268, 1997.

Sun, G., et al., "A New Cyclic N–Halamine Biocidal Polymer," *Ind. Eng. Chem. Res.* 33(1):168–170, 1994.

Sun, G., et al., "Disinfection of Water by N–Halamine Biocidal Polymers," *Ind. Eng. Chem. Res.* 34(11):4106–4109, 1995.

Sun, G., et al., "Performance of a New Polymeric Water Disinfectant," *Water Resources Bulletin* 32(4):793–797, Aug. 1996.

Tiller, J.C., et al., "Designing Surfaces That Kill Bacterial on Contact," *PNAS USA* 98(11):5981–5985, May 22, 2001.

Tsao, T.–C., et al., "Novel N–Halamine Disinfectant Compounds," *Biotechnol. Prog.* 7(1):60–66, 1991.

Worley, S.D., and G. Sun, "Biocidal Polymers," *TRIP* 4(11):364–370, Nov. 1996.

Worley, S.D., and J.F. Williams, "Disinfection of Water by N–Halamine Biocidal Polymers," *Water Conditioning & Purification* 39:96–100, Jul. 1997.

\* cited by examiner

R-Si(OR$_a$)$_3$  Alkoxysilane  (R$_a$ = alkyl)
↓ Hydrolysis/condensation
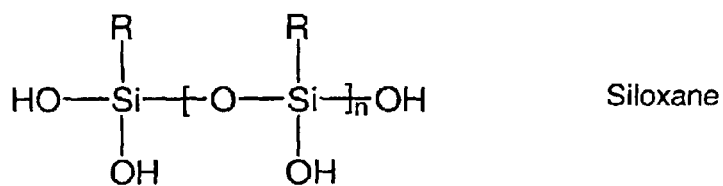 Siloxane
↓
OH  OH
|    |
———————  Substrate
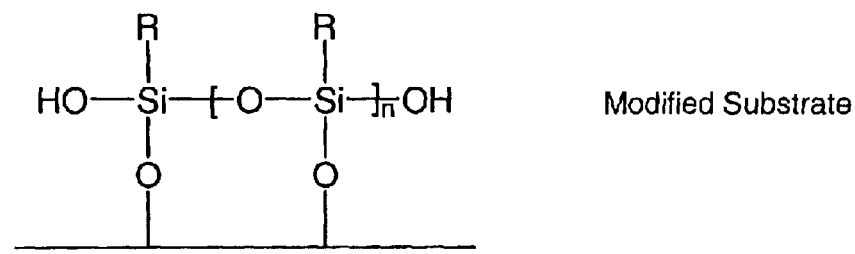 Modified Substrate
R = N-Halamine, Heterocyclic Amine, or Acyclic Amine
FIGURE

N-HALAMINE SILOXANES FOR USE IN BIOCIDAL COATINGS AND MATERIALS

CROSS-REFERENCE TO RELATED APPLICATION

This application claims the benefit of pending U.S. Provisional Application No. 60/388,968, filed on Jun. 14, 2002, incorporated herein expressly by reference in its entirety.

GOVERNMENT LICENSE RIGHTS

The U.S. Government has a paid-up license in this invention and the right in limited circumstances to require the patent owner to license others on reasonable terms as provided for by the terms of Grant No. F08637-01-C-6004 awarded by the United States Air Force.

FIELD OF THE INVENTION

The present invention relates to the synthesis and use of silane and siloxane compounds for the purpose of constructing coatings and materials which can be rendered biocidal by exposure to halogen solutions either before or after curing the coating or material. The biocidal coatings and materials can then be used to inactivate pathogenic microorganisms such as bacteria, fungi, and yeasts, as well as virus particles, that can cause infectious diseases, and those microorganisms that cause noxious odors and unpleasant coloring such as mildew. The coatings are compatible with a wide variety of substrates including cellulose, chitin, chitosan, synthetic fibers, glass, ceramics, plastics, rubber, cement grout, latex caulk, porcelain, acrylic films, vinyl, polyurethanes, silicon tubing, marble, metals, metal oxides, and silica.

BACKGROUND OF THE INVENTION

Previous attempts to incorporate biocidal activity into materials and coatings have primarily involved two methods: (1) physical mixing (blending) of biocides into the materials and coatings, and (2) chemical binding of biocidal functional groups to the polymers or copolymers comprising the materials and coatings. Chemical binding should be preferable for long-term biocidal activity if the bound biocidal functionality does not adversely affect the other desired properties such as strength, appearance, and chemical resistance of the material or coating. For example, a significant amount of work has been performed concerning rendering sponges biocidally active. This involves encapsulation of a variety of weak biocides into the porous structure of the sponge, either through physical blending or chemical bonding to the surface. The sponges modified in this manner can exhibit biocidal activity, but the contact times necessary for action are generally long, and some pathogens are not inactivated even at contact times of several hours. Antifouling polyurethanes have been prepared by chemical incorporation of tributyl tin as described in U.S. Pat. No. 5,194,504 and quaternary ammonium salts (see, for example, *J. Appl. Polym. Sci.* 50:663 (1993) and *J. Appl. Polym. Sci.* 50:671 (1993)). Coatings containing organo tin compounds are being discredited as threats to the environment, and poly-quats are weak biocides that are non-regenerable. Thus, there is a definite need for more effective biocidal coatings and materials.

A new class of biocidal monomers and polymers known as N-halamines, which could be useful in producing biocidal coatings, has recently been developed. A non-toxic, non-irritating, and cost effective material, poly-1,3-dichloro-5-methyl-5-(4'-vinylphenyl) hydantoin, is an inexpensive derivative of polystyrene, that was first described in U.S. Pat. No. 5,490,983. Subsequent disclosures of its biocidal properties for use in disinfecting applications for water filters have recently occurred (see, for example, *Ind. Eng. Chem. Res.* 33:168 (1994); *Water Res. Bull.* 32:793 (1996); *Ind. Eng. Chem. Res.* 34:4106 (1995); *J. Virolog. Meth.* 66:263 (1997); *Trends in Polym. Sci.* 4:364 (1996); *Water Cond. & Pur.* 39:96 (1997)). The polymer is effective against a broad spectrum of pathogens including *Staphylococcus aureus, Pseudomonas aeruginosa, Escherichia coli, Candida albicans, Klebsiella terrigena*, poliovirus, and rotavirus, among others, causing large log reductions in contact times of the order of a few seconds in water disinfection applications.

N-halamine functional groups such as hydantoins, oxazolidinones, and imidazolidinones have also been employed recently in producing biocidal cellulose (U.S. Pat. No. 5,882,357), biocidal films on surfaces (U.S. Pat. No. 5,902,818), biocidal Nylon (U.S. patent application Ser. No. 09/615,184), and biocidal polyester (U.S. patent application Ser. No. 09/866,535); these patents and patent applications are herein expressly incorporated by reference in their entirety.

U.S. Pat. No. 4,412,078 to Berger describes alkyl and alkoxy silylpropylhydantoin derivatives. Also, silylpropylisocyanurates have been reported for use as adhesive sealants (U.S. Pat. No. 3,821,218.) Moreover, much work has been done concerning attaching quaternary ammonium functional groups which are weak, non-regenerable biocides to various silicon compounds which can then be bonded to surfaces to render them weakly biocidal (see, for example, U.S. Pat. Nos. 3,560,385; 3,730,701; 3,794,736; 3,814,739; 3,860,709; 4,411,928; 4,282,366; 4,504,541; 4,615,937; 4,692,374; 4,408,996; 4,414,268; and 5,954,869). The N-halamine derivatives of the invention represent a significant improvement in biocidal efficacy over prior art in terms of both the required contact times and increased spectrum of activity.

SUMMARY OF THE INVENTION

Compounds according to the present invention have the following structures:

(1)

(2)

(3)

(4)

(5)

(6)

-continued

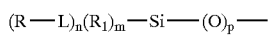 (7)

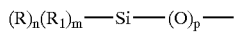 (8)

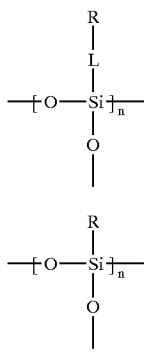

(9)

(10)

For structures (1)–(8) above, R1, R2, and R3 are independently selected from a C1–C4 alkyl, aryl, C1–C4 alkoxy, hydroxy, chloro, or C1–C4 ester group, wherein at least one of R1, R2, or R3 group is a C1–C4 alkoxy, hydroxy, chloro, or C1–C4 ester group; m=0, 1, or 2; n=1, 2, or 3 for structures (1), (3), (7), and (8); p=1, 2, or 3; m+n+p=4; and R is defined below.

L is a linker group that attaches R to the Si moiety. L is a linker alkylene, amine, or ether group, comprised of 1–13 carbons, 0–3 nitrogen or oxygen atoms, or L is a linker alkylene group of 1–13 carbons and a carbamate, thiocarbamate, or urea functional group.

R groups suitable for structures (1), (2), (5), (7), and (9) above are groups (11)–(21).

Imide-Linked Hydantoin

Imide-Linked Hydantoin

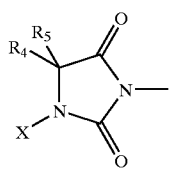 (11)

wherein R4 and R5 are independently selected from a C1–C4 alkyl, aryl, or hydroxymethyl group; and wherein X is at least one of chlorine or bromine. X can be hydrogen if the compound is represented by structures (5), a siloxane or (9), a modified substrate.

Amide-linked Hydrantoin

Amide-Linked Hydantoin

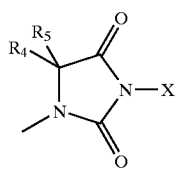 (12)

wherein R4 and R5 are independently selected from a C1–C4 alkyl, aryl, or hydroxymethyl group; and wherein X is at least one of hydrogen, chlorine or bromine.

Representative compounds having group (11) or (12) are those wherein R1, R2, R3 are independently selected from a methyl, ethyl, phenyl, methoxy, ethoxy, or hydroxy group; wherein at least one of R1, R2, or R3 is a methoxy, ethoxy, or hydroxy group; and wherein R4 and R5 are independently selected from a methyl, ethyl, hydroxymethyl or phenyl group.

Representative compounds having group (11) or (12) are those wherein R1, R2, and R3 are a methoxy or ethoxy group; R4 and R5 are a methyl group, and L is a linker alkylene, amine, or ether group, comprised of 1–7 carbons and 0–1 nitrogen or oxygen atoms, or L is a linker alkylene group, comprised of 1–7 carbons and a carbamate, thiocarbamate, or urea functional group.

Representative compounds having group (11) or (12) are those wherein R1, R2, R3 are a methoxy group; X is chlorine; and L is a linker alkylene comprised of 3 carbons.

Representative compounds having group (11) or (12) are those wherein R1, R2, R3 are a methoxy group; X is bromine; and L is a linker alkylene comprised of 3 carbons.

Representative compounds having group (11) or (12) are those wherein R1, R2, and R3 are an ethoxy group; X is chlorine; and L is a linker alkylene comprised of 3 carbons.

Representative compounds having group (11) or (12) are those wherein R1, R2, and R3 are an ethoxy group; X is bromine; and L is a linker alkylene comprised of 3 carbons.

Representative compounds having group (11) or (12) are those wherein R1, R2, and R3 are a methoxy group; X is chlorine; and L is a linker amine or ether group comprised of 4 carbons, and 1 nitrogen or oxygen atom.

Representative compounds having group (11) or (12) are those wherein R1, R2, and R3 are a methoxy group; X is bromine; and L is a linker amine or ether group comprised of 4 carbons, and 1 nitrogen or oxygen atom.

Representative compounds having group (11) or (12) are those wherein R1, R2, and R3 are an ethoxy group; X is chlorine; and L is a linker amine or ether group comprised of 4 carbons, and 1 nitrogen or oxygen atom.

Representative compounds having group (11) or (12) are those wherein R1, R2, and R3 are an ethoxy group; X is bromine; and L is a linker amine or ether group comprised of 4 carbons, and 1 nitrogen or oxygen atom.

Representative compounds having group (11) or (12) are those wherein R1, R2, and R3 are a methoxy group; X is chlorine; and L is a linker alkylene group comprised of 4 carbons and a carbamate, thiocarbamate, or urea functional group.

Representative compounds having group (11) or (12) are those wherein R1, R2, and R3 are a methoxy group; X is bromine; and L is a linker alkylene group comprised of 4 carbons and a carbamate, thiocarbamate, or urea functional group.

Representative compounds having group (11) or (12) are those wherein R1, R2, and R3 are an ethoxy group; X is chlorine; and L is a linker alkylene group comprised of 4 carbons and a carbamate, thiocarbamate, or urea functional group.

Representative compounds having group (11) or (12) are those wherein R1, R2, and R3 are an ethoxy group; X is bromine; and L is a linker alkylene group comprised of 4 carbons and a carbamate, thiocarbamate, or urea functional group.

Imidazolidinone

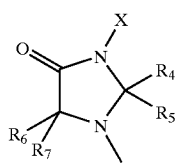
(13)

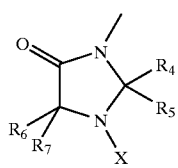
(14)

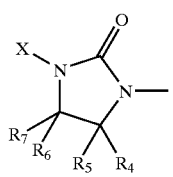
(15)

wherein R4, R5, R6, and R7 are independently selected from a C1–C4 alkyl, aryl, or hydroxymethyl group; and wherein X is at least one of hydrogen, chlorine, or bromine.

Representative compounds having group (13), (14), or (15), are those wherein R1, R2, and R3 are a methoxy, ethoxy, or hydroxy group; R4, R5, R6, and R7 are a methyl group; and L is a linker alkylene, amine, or ether group, comprised of 1–4 carbons, and 0–1 nitrogen or oxygen atoms, or L is a linker alkylene group, comprised of 1–4 carbons, and a carbamate, thiocarbamate, or urea functional group.

Oxazolidinone

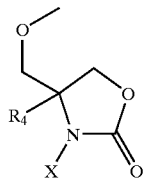
(16)

wherein R4 is at least one of a C1–C4 alkyl, aryl, or hydroxymethyl group; and wherein X is at least one of hydrogen, chlorine, or bromine.

Representative compounds having group (16) are those wherein R1, R2, and R3 are a methoxy, ethoxy, or hydroxy group; R4 is a methyl, ethyl, or hydroxymethyl group; and L is a linker alkylene group, comprised of 1–3 carbons, or L is a linker alkylene group, comprised of 1–3 carbons, and a carbamate, thiocarbamate, or urea functional group.

Glycoluril

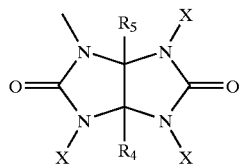
(17)

wherein R4 and R5 are independently selected from a C1–C4 alkyl, aryl, or hydroxymethyl group; and wherein X is independently selected from at least one of hydrogen, chlorine, bromine, or hydroxymethyl; and wherein at least one X is hydrogen, chlorine, or bromine.

Representative compounds having group (17) are those wherein R1, R2, and R3 are a methoxy, ethoxy, or hydroxy group; R4 and R5 are a methyl group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbamate, or urea functional group.

Isocyanurate

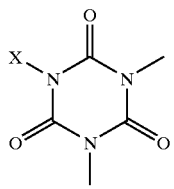
(18)

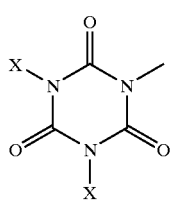
(19)

wherein X is independently selected from at least one of hydrogen, chlorine, bromine, or hydroxymethyl; and wherein at least one X is hydrogen, chlorine, or bromine.

Representative compounds having group (18) or (19) are those wherein R1, R2, and R3 are a methoxy, ethoxy, or hydroxy group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbamate, or urea functional group.

Triazinedione

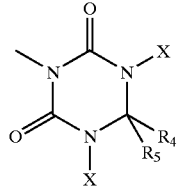
(20)

wherein R4 and R5 are independently selected from a C1–C4 alkyl, aryl, or hydroxymethyl group; and wherein X is independently selected from at least one of hydrogen, chlorine, bromine, or hydroxymethyl; and wherein at least one X is hydrogen, chloride, or bromine.

Representative compounds having group (20) are those wherein R1, R2, and R3 are a methoxy, ethoxy, or hydroxy group; R4 and R5 are a methyl group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbamate, or urea functional group.

Piperidine

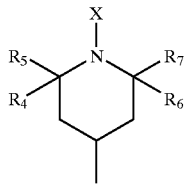

(21)

wherein R4, R5, R6, and R7 are independently selected from a C1–C4 alkyl, aryl, or hydroxymethyl group; and wherein X is chlorine or bromine when on structure (1) or (2), but X is hydrogen, chlorine, or bromine when on structures (5), (7), or (9).

Representative compounds having group (21) are those wherein R1, R2, and R3 are a methoxy, ethoxy, or hydroxy group; R4, R5, R6, and R7 are a methyl group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbamate, or urea functional group.

R groups suitable for structures (3) (4) (6) (8) and (10) are an amino alkylene or a polyamino alkylene group comprising at least one N-chloro or N-bromo group. A representative group for structures (3) (4) (6) (8) and (10) is an amino propyl group.

For groups (5) (6) (9) and (10), n, is the number of repeating units, not to be confused with n of structures (1) (3) (6) and (7) where, n, is the number of R moieties on Si. The repeating number of units, n, is greater than or equal to 2. However, n, can be as much as 500, or greater.

A method for making a modified substrate, comprises applying a solution of a compound of structure (1), and water, to a substrate; drying the solution and curing the substrate at an elevated temperature to provide a modified substrate, wherein R in structure (1) is a heterocyclic N-Halamine. The solution can further comprise an alcohol. Alternatively, the solution can be an alkaline solution.

A method for making a modified substrate, comprises applying a solution of a compound of structure (1), and water, to a substrate; drying the solution; and curing the substrate at an elevated temperature to provide a modified substrate, wherein R in structure (1) is a heterocyclic amine from at least an amide-linked hydantoin, imidazolidinone, oxazolidinone, isocyanulate, glycoluril, and triazinedione.

A method for making a modified substrate, comprises applying a solution of a silane having a pendant heterocyclic amine, and water, to a substrate; drying the solution; curing the substrate at an elevated temperature; and halogenating the heterocyclic amine with an oxidative halogen compound to provide a modified substrate.

A method for making a modified substrate, comprises applying a solution of a compound of structure (3), and water, to a substrate; drying the solution; and curing the substrate at an elevated temperature to provide a modified substrate.

A method for making a modified substrate, comprises applying a solution of a silane having a pendant aminoalkylene or polyamino alkylene group, and water, to a substrate; drying the solution; curing the substrate at an elevated temperature; and halogenating the amino group with an oxidative halogen compound to provide a modified substrate.

A method for making a modified substrate, comprises applying a solution of a compound of structure (5), and water, to a substrate; drying the solution; and curing the substrate at an elevated temperature to provide a modified substrate, wherein R in the structure (5) is a heterocyclic N-halamine.

A method for making a modified substrate, comprises applying a solution of a siloxane of structure (5), and water, to a substrate; drying the solution; and curing the substrate at an elevated temperature to provide a modified substrate, wherein R in the structure (5) is a heterocyclic amine from at least an amide-linked hydantoin, imidazolidinone, oxazolidinone, isocyanurate, glycoluril, triazinedione, and piperidine.

A method for making a modified substrate comprises applying a solution of a siloxane having a pendant heterocyclic amine, and water, to a substrate; drying the solution; curing the substrate at an elevated temperature; and halogenating the heterocyclic amine with an oxidative halogen compound to provide a modified substrate.

A method for making a modified substrate, comprises applying a solution of a siloxane of structure (6), and water, to a substrate; drying the solution; and curing the surface at an elevated temperature to provide a modified substrate.

A method for making a modified substrate, comprises applying a solution of a siloxane having a pendant amino alkylene or polyamino alkylene group, and water, to a substrate; drying the solution; curing the substrate at an elevated temperature; and halogenating the amino group with an oxidative halogen compound.

The present invention provides numerous advantages, including the ability of rendering surfaces and materials biocidal when the compounds of the invention are bound thereto, and the amine moiety has an N-chloro or an N-bromo group.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

The sole FIGURE is an illustration of one embodiment of a reaction mechanism for modifying a substrate according to the present invention.

DETAILED DESCRIPTION OF THE PREFERRED EMBODIMENT

The present invention may be understood more readily by reference to the following detailed description of specific embodiments and the examples included therein.

A silane or silane compound can be a monomer to produce polymers or siloxanes. The silanes and siloxanes have heterocyclic and acyclic amine moieties. The heterocyclic amine moieties are bound by a linker group. The heterocyclic and acyclic amine moieties can impart biocidal functionality when the moieties have an N-chloro or an N-bromo group. The silanes and siloxanes can be bound to substrates, and the substrates rendered biocidal. A siloxane compound can be an oligomer or polymer.

As used herein, "the modified substrate" refers to a surface or material to which a silane or siloxane compound having the structure (1), (2), (3), (4), (5), or (6) has been attached through one or more of the moieties $R_1$, $R_2$, and $R_3$. If X in the amine group is Cl or Br or combinations thereof, the surface or material will be biocidal; if X in the amine group is H, the surface or material will not be biocidal, but the surface or material can be rendered biocidal by exposing it to a source of oxidative chlorine or bromine. The substrates are represented by structures (7), (8), (9), and (10).

The unhalogenated silane compound of the invention can be synthesized by reacting a heterocyclic amine with a base in a solvent, such as ethanol, followed by reaction of the resulting alkali metal salt with a haloalkylsilane in a solvent such as anhydrous dimethylformamide (DMF) such that the linker L constitutes an alkylene group.

Alternatively, an unhalogenated silane compound of the invention can be prepared by reacting a heterocyclic amine containing a hydroxymethyl substituent with an aminoalkylsilane, a haloalkylsilane, an isocyanatoalkylsilane, an isothiocyanatoalkylsilane, or a silyl urea in a solvent such as anhydrous dimethylformamide such that the linker L constitutes an amine or an ether moiety, an alkylene carbamate, an alkylene thiocarbamate, or an alkylene urea, respectively. Alternatively, the unhalogenated silane compound of the invention can be an alkyleneamino or alkylenepoly-amino silane itself to which no heterocyclic amine is attached. In general, the raw materials used in the synthesis of the silane compounds of the invention are inexpensive and available commercially from vendors such as Aldrich Chemical Company (Milwaukee, Wis.), Fisher Scientific (Pittsburgh, Pa.), Gelest Inc. (Tullytown, Pa.), Acros, Inc. (Pittsburgh, Pa.), and TCI America (Portland, Oreg.).

For group 11, for example, 5,5-dimethylhydantoin can first be reacted with potassium hydroxide in ethanol, followed by reaction of the potassium salt of the hydantoin with chloropropyltrimethoxysilane in anhydrous dimethylformamide to produce 5,5-dimethyl-3-trimethoxysilylpropylhydantoin according to the method of Berger in U.S. Pat. No. 4,412,078. All of the starting reagents necessary to make this monomer are available commercially.

For group 13, for example, 2,2,5,5-tetramethyl-1,3-imidazolidin-4-one, prepared according to U.S. Pat. No. 5,057,612, can be treated with the mild base sodium carbonate to neutralize the hydrochloric acid produced upon reaction of chloropropyltrimethoxysilane at the amine position on the imidazolidinone ring.

For group 14, the strong base, potassium hydroxide can be used to form the potassium salt at the amide nitrogen of the imidazolidinone ring in xylene as a solvent as in U.S. Pat. No. 4,448,969, followed by reaction with the chloropropyltrimethoxysilane.

For group 16, 4-ethyl-4-hydroxymethyloxazolidinone, prepared according to U.S. Pat. No. 5,902,818, can be reacted with sodium metal to produce the sodium salt at the oxygen bonded to the exocyclic methylene group, followed by a nucleophilic substitution reaction with chloropropyltrimethoxysilane.

For groups 15 and 17, each possessing amide nitrogens, representatives can be produced by reacting 4,4,5,5-tetramethyl-1,3-imidazolidin-2-one, prepared according to U.S. Pat. No. 4,681,948, and dimethylglycoluril, available commercially, respectively, with potassium hydroxide, followed by reaction with chloropropyltrimethoxysilane as for the group 14 case.

For groups 18, 19 and 20, possessing reactive imide nitrogen moieties, the unhalogenated silane compounds can be made, for example, in a procedure analogous to that for the silylhydantoin in group 11 by reacting a sodium or potassium salt of the isocyanurate (available commercially) or a triazinedione (prepared in analogous manner to a derivative described in U.S. Pat. No. 5,490,983), respectively, with chloropropyltrimethoxysilane. In the case of the isocyanurate of group 18, two equivalents of chloropropyltrimethoxysilane can be used to bond the trimethoxysilylpropyl moiety to two of the nitrogens of the triazine ring, leaving one nitrogen free for reaction with halogen.

For group 12, two equivalents of a strong base, such as sodium hydride, can be employed to produce the disodium salt of the hydantoin, followed by reaction with one equivalent of chloropropyltrimethoxysilane, to produce a mixture of the compounds of groups 11 and 12.

For group 21, the general procedure described in U.S. Pat. No. 4,684,726 can be followed to produce, for example, 3-(2,2,6,6-tetramethylpiperidine-4-oxy)propyltriethoxysilane.

The silane compounds can be rendered biocidal by reacting the corresponding unhalogenated silane compounds, dissolved in water, at ambient temperature with free chlorine from such sources as gaseous chlorine, sodium hypochlorite bleach, calcium hypochlorite, chloroisocyanurates, and dichlorohydantoins. In the case of the dichlorohydantoins, the chlorine moiety on the imide nitrogen should transfer to the more stable amide nitrogen, if available. Likewise, the brominated silane compounds can be prepared by exposing them in aqueous solution at ambient temperature to free bromine from such sources as molecular bromine liquid, sodium bromide in the presence of an oxidizer such as potassium peroxy monosulfate, and brominated hydantoins. Halogenation can also be effected in organic solvents employing free radical halogenating agents such as t-butyl hypochlorite.

The unhalogenated or halogenated silane compounds can be bound or immobilized to a surface or material through either covalent bonding or an adhesive interaction depending on the nature of the surface or material to provide a surface modified with the unhalogenated or halogenated silane compounds. This can be accomplished by exposing the surface or material to a solution of the unhalogenated silane compound at temperatures in the range of 0 to 300° C., more preferably 20 to 150° C., depending upon the nature of the surface or material. Immobilization of the halogenated silane compounds can be accomplished by exposing the surface or material to a solution of the compound at temperatures in the range of 0 to 60° C., more preferably, 20 to 40° C., depending upon the nature of the surface or material. The solvent for the silane compounds should contain at least 50% water to be used in the conversion of any alkoxy groups (comprising the $R_1$, $R_2$, and $R_3$ groups in structure II) to hydroxyl groups so as to provide binding sites to the surface or material. Organic solvents such as dimethylsulfoxide, tetrahydrofuran, dimethylformamide, alcohols, acetone, ethyl acetate, and methylene chloride can also be used in conjunction with water for the silane compounds, although alcohols are less useful for the halogenated silane compounds because they partially protonate the nitrogen of the heterocyclic ring or alkyleneamino group liberating halogen. Base can also be added to the aqueous solutions to enhance the solubility of the silane compounds. If water is the only solvent used, the pH should be adjusted to greater than 12. Other additives can be introduced to the solutions of the silane compounds to enhance binding to the surface or materials, e.g., potassium thiocyanate for binding to cellulose. The solutions containing the silane compounds can be exposed to the surfaces or materials by soaking, spraying, spreading, and the like. Following drying of the solution on the surface, curing at some temperature (which depends upon the surface or material composition, e.g., 25° C. for paper, 95° C. for cotton fibers and glass) for 15 to 30 minutes, should be performed.

The unhalogenated or halogenated silane compounds can also be polymerized to form siloxane compounds before attaching them to surfaces by exposing them to an acid such as hydrochloric acid in mixtures of ethanol and water, or water alone. The reaction is illustrated in the FIGURE. The heterocyclic moieties can be introduced before or after the polymerization.

The surface or material can be rendered biocidal if the unhalogenated silane or siloxane compounds are immobilized on the surface by exposure to a source of oxidative halogen, such as an aqueous solution of sodium hypochlorite bleach, calcium hypochlorite, chloroisocyanurates, and dichlorohydantoins; or an organic solution of t-butyl hypochlorite, for chlorination, or an aqueous solution of molecular bromine liquid, sodium bromide in the presence of an oxidizer such as potassium peroxy monosulfate, and brominated hydantoins for bromination. For example, an aqueous solution of 10% CLOROX can be used for efficient chlorination which can be accomplished at ambient temperature by spraying or soaking the surface or material with same. After halogenation, the surface or material should be allowed to dry in air at temperatures up to 40° C. (ambient temperature is preferable if time permits) and rinsed with water. The modified surface or material will then exhibit biocidal properties for various time periods dependent upon the composition of the surface or material, the use pattern (contact with organisms and halogen demand), and the storage temperature. When the bound halogen content becomes too low for efficient biocidal activity, the modified surface or material can be recharged with halogen in the same manner as for the original charging noted above.

An alternate embodiment of attaching the biocidal moieties to surfaces is to first bond a silane or a siloxane compound containing a substituted nucleophilic alkyl functional group to the surface, and second, bonding the heterocyclic N-halamine or heterocyclic amine group to the tethered silane or siloxane through a nucleophilic substitution reaction. For example, aminopropyltriethoxysilane can be bonded to a surface, and then the amino functionality can be reacted with 3-hydroxymethylhydantoin to produce an anchored hydantoin that can then be halogenated in situ as described above to render the surface biocidal. Alternatively, the tethered aminopropyltriethoxysilane could be directly halogenated in situ as described above to achieve a biocidal surface. In general, the halogen will be stabilized to a greater extent when bonded to nitrogen on a heterocyclic moiety as opposed to an acyclic moiety.

The mechanism of action of the biocidal surfaces and materials produced as described herein is believed to be a result of surface contact of the organism with chlorine or bromine covalently bound to the heterocyclic functional groups on the bound silane. The chlorine or bromine atoms are transferred to the cells of the microorganisms where they cause inactivation through a mechanism not completely understood, but probably involving oxidation of essential groups contained within the enzymes comprising the organisms.

A marked advantage of the biocidal surfaces and materials of this invention over prior technology is that the surfaces and materials are much more effective biocidally against pathogenic microorganisms, such as Staphylococcus aureus and Pseudomonas aeruginosa, encountered in medical applications than are commercial biocides such as the quaternary ammonium salts. The biocidal surfaces and materials serve a dual function: (1) inactivation of disease-causing pathogens, and (2) inactivation of odor-causing microorganisms. For this reason, the invention will have widespread use in medical settings such as hospitals, nursing facilities, and research laboratories. It should also be useful for biocidal applications in a variety of other industrial settings, as well as in the home.

Representative surfaces and materials that can be made biocidal with this invention include envelopes, surgical gowns and gloves, sheets, bandages, sponges, table and counter tops, glassware, as well as articles made from plastic, synthetic fibers, wood, chitin, chitosan, cement grout, latex caulk, porcelain, acrylic films, vinyl, polyurethanes, silicon tubing, marble, and metals.

EXAMPLES

Example 1

Preparation of a Representative Unhalogenated Silane Compound

Two trialkoxysilylpropylhydantoin derivatives were prepared according to a procedure similar to that outlined in U.S. Pat. No. 4,412,078.

A one-liter, three-neck-round-bottom flask was fit with a condenser, dropping funnel, and thermometer. To the flask was added a mixture of 500 mL of ethanol, 64.0 g (0.5 mol) of 5,5-dimethylhydantoin (Acros, Inc.), and 28.0 g (0.5 mol) of potassium hydroxide. The mixture was heated to the boiling point until the solution became clear. Then the solid potassium salt of the 5,5-dimethylhydantoin was isolated by evaporation of the ethanol solvent and the water produced in the reaction under reduced pressure. This salt was dried under vacuum at 60° C. for four days to form the anhydrous potassium salt. The dry salt was then placed back in the one liter flask where it was mixed with 500 mL of anhydrous N,N-dimethylformamide (DMF), and the mixture was heated at 60° C. until a clear solution formed. Then 120.4 g (0.5 mol) of 3-chloropropyltriethoxysilane (Aldrich Chemical Company) were added dropwise over a one-hour period with stirring at ambient temperature. The mixture was then heated at 95° C. for 4 hours, cooled, and the potassium chloride produced in the reaction was removed by filtration. The DMF solvent was removed by distillation to produce 150.0 g of a brown, viscous oil identified as 3-triethoxysilylpropyl-5,5-dimethylhydantoin, the yield being 90.3% of theoretical. The product was further purified by distillation under reduced pressure (16 mm Hg, fraction collected 235–238° C.) for elemental and spectroscopic characterization. Anal. Calcd. for $C_{14}H_{28}SiN_2O_5$: C, 50.6; H, 8.4; N, 8.4. Found: C, 50.3; H, 8.4; N, 9.0. $^1$H NMR (CDCl$_3$) ∂ 0.61 (2H), 1.22 (9H), 1.43 (6H), 1.73 (2H), 3.48 (2H), 3.82 (6H), 7.17 (1H). IR (KBr) 740, 813, 1081, 1104, 1713, 1774, 2879, 2989, 3279, 3485 cm$^{-1}$. MS (CI/CH$_4$) m+1, 333.

A procedure analogous to that described above utilizing 3-chloropropyltrimethoxysilane (Aldrich Chemical Company) provided 3-trimethoxysilylpropyl-5,5-dimethylhydantoin as a brown oil (8 mm Hg, fraction collected 194–195° C.), the yield being 92.0% of theoretical. $^1$H NMR (CDCl$_3$) ∂ 0.62 (2H), 1.43 (6H), 1.71 (2H), 3.53 (11H), 7.07 (1H). IR (KBr) 740, 812, 1091, 1450, 1712, 1773, 2835, 2959, 3000–3400 cm$^{-1}$.

Example 2

Preparation and Biocidal Efficacy of a Representative Chlorinated Silane Compound A portion (6.11 g, 0.021 mol) of 3-trimethoxysilylpropylhydantoin, prepared as described in Example 1, was dissolved in 30 mL of methylene chloride in a 125 mL Erlenmeyer flask. Then 2.30 g (0.021 mol) of tert-butyl hypochlorite, prepared according to the method of Mintz, et al. (*Org. Syn.* 1969, 49:9–12), were added at room temperature, and the flask was stoppered, and the mixture was allowed to stand at room temperature for 3 hours with all light excluded. Vacuum evaporation was employed to remove the tert-butyl alcohol produced in the reaction. The product, 1-chloro-3-trimethoxysilylpropyl-5,5-dimethylhydantoin, was produced as a yellow oil in 89.7% yield. It was stored at 4° C. in the absence of light until use. The total chlorine content was determined to be 10.36% by iodometric/thiosulfate titration as compared to the theoretically possible value of 10.94%. The $^1$H NMR signal at $\delta$ 7.07 for 3-trimethoxysilylpropylhydantoin vanished upon chlorination indicating the presence of chlorine at the 1 position of the hydantoin moiety.

A 100.8 mg/L solution of the chlorinated silane compound, prepared as described above, containing 11.02 mg/L total chlorine content in chlorine-demand-free water at pH 7 was challenged with *S. aureus* bacteria (ATCC 6538) for contact times of 5, 10, 30, and 60 min at ambient temperature. Following the contact with the bacteria, further disinfectant action was quenched by adding 0.02 N sodium thiosulfate. Serial dilutions were then plated onto trypticase soy agar, and colony counts were made after 48 hours of incubation at 37° C. No growth was detected on the plates indicating a complete inactivation (>4.9 logs) at all of the contact times. Thus the chlorinated silane compound is biocidal under the conditions tested. Neither lower contact times, nor lower concentrations, were evaluated.

Example 3

Preparation of Biocidal Paper

Small pieces of white and brown commercial office envelopes were cut into small squares. A 2% aqueous alkaline solution (pH 3 from NaOH addition) of 3-triethoxysilylpropyl-5,5-dimethylhydantoin, prepared as described in Example 1, was sprayed from an atomizer bottle onto both sides of the paper samples until they became saturated. Then the wet samples were cured until dry at 60° C. for 15 minutes. The cured samples were then sprayed on both sides with 10% CLOROX bleach until saturated, allowed to stand at ambient temperature for 10 minutes, rinsed 5 times with 50 mL portions of chlorine-demand-free water, and dried at ambient temperature. The samples were stored in a vacuum desiccator until use for analytical and microbiological characterization.

An iodometric/thiosulfate titration procedure was used to determine the chlorine loadings on the squares of the two kinds of paper as a function of time after chlorination. The data are shown in Table 1.

TABLE 1

STABILITY OF CHLORINE ON PAPER SAMPLES

| Sample Type | Time Since Chlorination (d) | % Cl Loading | mg/cm$^2$ Cl Loading |
|---|---|---|---|
| White | 0 | 0.823 | 0.055 |
| White | 14 | 0.82 | 0.049 |
| White | 21 | 0.79 | 0.047 |
| White | 28 | 0.79 | 0.0454 |
| White | 36 | 0.781 | 0.0448 |
| Brown | 0 | 0.51 | 0.0344 |
| Brown | 14 | 0.50 | 0.032 |
| Brown | 21 | 0.499 | 0.034 |
| Brown | 28 | 0.488 | 0.033 |
| Brown | 36 | 0.464 | 0.032 |

From the data in Table 1, it can be concluded that the treated paper samples stabilized chlorine very well over a 36-day period.

Freshly chlorinated paper samples (white and brown) were also challenged with *S. aureus* bacteria (ATCC 6538). Control samples consisted of treated, but unchlorinated paper, and untreated, but chlorinated paper. The data are presented in Table 2.

TABLE 2

INACTIVATION OF *S. AUREUS* BY PAPER SAMPLES

| Sample Type | 1 Min Log Reduction | 5 Min Log Reduction | 10 Min Log Reduction | 30 Min Log Reduction |
|---|---|---|---|---|
| White Contr | 0 | 0 | 0 | 0 |
| White Cl | 0.1 | 3.0 | >5.4[a] | >5.4 |
| Brown Contr | 0 | 0 | 0 | 0 |
| Brown Cl | 1.9 | 4.6 | >5.3 | >5.3 |

[a]The > indicates that no surviving colonies could be detected.

From the data in Table 2, it can be concluded that both kinds of treated paper were effective in killing the bacteria. An untreated control which was subjected to the same chlorination procedure produced a reduction of about 1 Log during a 1 hour contact, but it is clear that most of the inactivation of the bacteria by the chlorinated treated samples can be attributed to the bound chlorine on the hydantoin moiety.

Similar results have been obtained for commercial paper file folders.

Example 4

Preparation of Biocidal Cotton

Swatches of Style 400 Bleached 100% Cotton Print Cloth (Testfabrics, Inc.) were treated with 3-triethoxysilylpropyl-5,5-dimethylhydantoin, prepared as described in Example 1, in the following manner. A treatment bath was prepared containing 5.0 g of 3-triethoxysilylpropyl-5,5-dimethylhydantoin, 3.0 g of potassium thiocyanate, 50 mL of ethanol, and 50 mL of water. After 1 hour of equilibration of the bath mixture, the cotton swatches were soaked in the bath for 10 min. After partially drying in air at ambient temperature, the swatches were cured for 1 hour at 95° C. The swatches were then soaked in a 0.5% liquid detergent solution for 15 min, rinsed with tap water, and allowed to dry in air at ambient temperature. It was found that this treatment produced an average percent weight gain of the swatches of 5.5±0.6%; for an identical treatment except with the omission of KSCN the average weight gain was 4.7±0.3%. The swatches were charged with chlorine by soaking in a 10% CLOROX solution for 30 min at ambient temperature, rinsed thoroughly with chlorine-demand-free water until test strips showed less than 0.2 mg/L of free chlorine in the wash water, and then dried in air at ambient temperature. It was found that the average chlorine loading on the swatches was 0.61±0.14%; without the use of KSCN the average chlorine loading was 0.49±0.07%. The swatches were stored in a vacuum desiccator until use.

For comparison purposes, a biocidal quaternary ammonium compound (dimethyloctadecyltrimethoxysilylpropylammonium chloride, Aldrich Chemical Company) was also used to treat cotton swatches in a bath similar to that described above (with and without KSCN). The average weight % add on was 14.7%.

Treated cotton swatches were challenged with *S. aureus* (ATCC 6538) and *Escherichia coli* (ATCC 2666) at a concentration of between $10^8$ and $10^9$ CFU/mL in pH 7 phosphate buffer solution using a modified version of AATCC Method 100. The swatches were quenched with 0.02 N sodium thiosulfate solution at contact times of 10, 30, 60, and 120 min. Serial dilutions of the solutions contacting the swatches were plated on nutrient agar, incubated for 48 hours at 37° C., and plate counts were made to determine the presence of viable bacteria. It was found that all *S. aureus* colonies (>5.7 logs) were inactivated by the swatches treated with 3-triethoxysilylpropyl-5,5-dimethylhydantoin (with or without KSCN in the treatment bath) in the contact time interval 10–30 minutes; whereas, the swatches treated with the quaternary ammonium salt experienced only a 1.8 log reduction at 30 minutes. The control sample (cotton soaked in 10% bleach, rinsed, and dried) gave only a 0.4 log reduction at 30 minutes. It was found that all *E. coli* (>5.9 logs) were inactivated by the swatches treated with 3-triethoxysilylpropyl-5,5-dimethylhydantoin (with or without KSCN in the treatment bath) in the contact time interval 60–120 minutes; whereas, the swatches treated with the quaternary ammonium salt experienced only a 2.5 log reduction in this contact time interval. The control sample (cotton soaked in 10% bleach, rinsed, and dried) gave a 0 log reduction at 120 minutes.

It can be concluded that cotton cloth treated with 3-triethoxysilylpropyl-5,5-dimethylhydantoin (with or without KSCN in the treatment bath) is biocidal. Furthermore, the hydantoin derivative is more effective than the biocidal quat, and it seems to be somewhat more effective against the Gram positive bacterium *S. aureus* than against the Gram negative bacterium *E. coli*.

Washing tests have demonstrated that the cotton cloth treated by the 3-triethoxysilylpropyl-5,5-dimethylhydantoin retains about 34% of its bound chlorine after 50 wash cycles. A 1% bleach solution can be used for chlorination if the time of contact is 30 minutes.

A stability test during dry storage was also conducted on cotton samples coated with 3-triethoxysilylpropyl-5,5-dimethylhydantoin. One half of the samples were coated in a bath containing 8% of the 3-triethoxysilylpropyl-5,5-dimethylhydantoin in 50% ethanol in water solution. The other half were treated in the same manner except that KSCN was added to the treatment bath as described above. The chlorination conditions and analytical method of measuring chlorine loadings were the same as discussed above. The samples were stored in plastic bags at ambient temperature; the bags were not air-tight. The average chlorine loading for the samples treated in the presence of KSCN declined from 0.776% to 0.680% over a period of 50 days. For the samples not treated in the presence of KSCN, the decline was from 0.620% to 0.540% over the same 50 day period. It can be concluded that the coated cotton samples were fairly stable to loss of chlorine in dry storage.

Finally, tensile strength tests were run on coated cotton fibers. It was found that the average decline in tensile strength upon coating the cotton fibers with 3-triethoxysilylpropyl-5,5-dimethylhydantoin was about 8.7%; chlorination caused a further loss of only 0.6%. In this case the measurements were made upon the day of chlorination. A further decline in strength would be expected with time after chlorination and with frequency of rechlorination, since bleaching is known to cause slow degradation in cotton fibers.

Example 5

Preparation and Testing of a Representative Siloxane Compound

A polymeric form of 3-chloropropylsiloxane was prepared as follows. In a 500 mL flask, 72.14 g (0.3 mol) of 3-chloropropyltriethoxysilane was mixed with 100 mL of ethanol, and while stirring the mixture, 77.8 g of concentrated hydrochloric acid were added dropwise. The mixture was then refluxed for 5 hours followed by removal of water and ethanol to produce a viscous oil. The oil was held at 80° C. under vacuum (about 30 mm Hg) for 15 hours. The polymer (41.0 g) was obtained in 99% yield per unit based upon the structure proposed below.

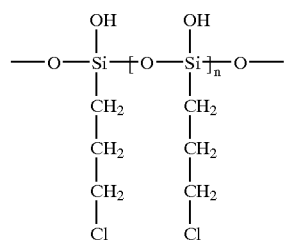

An elemental analysis based upon the proposed structure yielded: Calcd. for $C_3H_7SiO_2Cl$: C, 26.00; H, 5.05; Cl, 25.63. Found: C, 28.67; H, 4.85; Cl, 26.56. $^1$H NMR ($d_6$-DMSO) ∂0.76 (2H), 1.79 (2H), 3.33 (1H), 3.60 (2H).

Then the potassium salt of 5,5-dimethylhydantoin was prepared by slowly adding 14.98 g (0.267 mol) of potassium hydroxide to 34.21 g (0.267 mol) of 5,5-dimethylhydantoin in 100 mL of DMF with stirring in a 500 mL flask. The mixture was further stirred at ambient temperature for 30 minutes. Then 37.0 g (0.267 mol per unit) of the polymer of 3-chloropropylsiloxane in 100 mL of DMF were added to the mixture, which was held at 100° C. for 6 hours with stirring. The potassium chloride salt produced and the DMF solvent were removed by filtration and evacuation, respectively, to give 59.2 g crude yield (96.4%) of viscous oil. The viscous oil was further held at 150° C. under vacuum (about 30 mm Hg) for 8 hours. The polymer product was a white solid at ambient temperature produced in high yield based upon the structure proposed below.

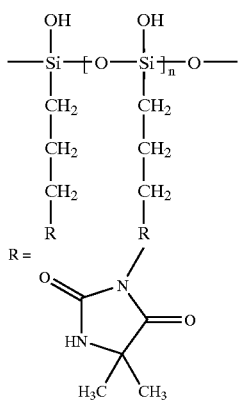

An elemental analysis based upon the proposed structure yielded: Calcd. for $C_8H_{14}SiN_2O_4$: C, 41.74; H, 6.09; N, 12.17; Cl, 0.00. Found: C, 41.69; H, 6.14; N, 12.03; Cl, <0.25. $^1$H NMR ($d_6$-DMSO) ∂ 0.52 (2H), 1.26 (6H), 1.52 (2H), 3.29–3.36 (3H), 8.16 (1H); IR (KBr) 774, 1122, 1281, 1352, 1422, 1452, 1709, 1772, 2935, 2977, 3000–3600 cm$^{-1}$. The infrared bands at 1709 and 1772 cm$^{-1}$ are indicative of the presence of the hydantoin ring in the siloxane polymer.

The siloxane polymer described above was coated onto 100% cotton fabric. This was accomplished by soaking swatches of the material for about 2 minutes at ambient temperature in a bath containing 5 g of the polysiloxane, 70 mL of ethanol, and 40 mL of water. The swatches were cured at 130° C. in air for 20 minutes, then soaked in 1.5% liquid detergent for 15 minutes at ambient temperature, and then rinsed thoroughly with water. After drying in air at 50° C. for 30 minutes, the swatches were then soaked in 5% CLOROX at ambient temperature for 45 minutes, rinsed thoroughly with water, and dried in air at 50° C. for 30 minutes to remove any free chlorine present. An iodometric/thiosulfate titration indicated a chlorine loading on the cotton material of about 0.42%.

A biocidal evaluation of representative cotton swatches using the procedure outlined in Example 4 showed that the treated material produced a 1.7 log reduction of *S. aureus* bacteria within a contact time range of 10–30 minutes, but a 7.6 log reduction (total inactivation) within the range of 30–60 minutes. Thus a longer contact time was required for the chlorinated siloxane polymer coating than for the silane monomer coating described in Example 4, but the chlorine loading was also lower by 14.3%, so this result was not unexpected.

TABLE 3

EFFECTS OF WASHING TESTS ON COTTON COATED SWATCHES

| Coating Type (Monomer, M) (Polymer, P) | Chlorination Before Washing | Chlorination After Washing | Washing Cycles | Average Chlorine Loading % |
|---|---|---|---|---|
| M | No | Yes | 5 | 0.26 |
| M | No | Yes | 10 | 0.15 |
| M | No | Yes | 50 | 0.03 |
| P | No | Yes | 5 | 0.21 |
| P | No | Yes | 10 | 0.18 |
| P | No | Yes | 50 | 0.05 |
| M | Yes | No | 5 | 0.42 |
| M | Yes | No | 10 | 0.41 |
| M | Yes | No | 50 | 0.10 |
| P | Yes | No | 5 | 0.25 |
| P | Yes | No | 10 | 0.20 |
| P | Yes | No | 50 | 0.13 |
| M | Yes | Yes | 5 | 0.394 |
| M | Yes | Yes | 10 | 0.388 |
| M | Yes | Yes | 50 | 0.133 |
| P | Yes | Yes | 5 | 0.263 |
| P | Yes | Yes | 10 | 0.247 |
| P | Yes | Yes | 50 | 0.146 |

Finally, a wash test was performed on swatches of cotton containing the monomer 3-triethoxysilylpropyl-5,5-dimethylhydantoin coating and the polysiloxane coating, each chlorinated and unchlorinated, for comparison purposes. Two treatment baths were prepared, one containing an 8% solution of 3-triethoxysilylpropyl-5,5-dimethylhydantoin in a 50% solution of ethanol in water, the other containing an 8% solution of siloxane polymer prepared as described above in a 66.7% solution of ethanol in water. Identical cotton swatches were soaked in the two baths for 2.5 minutes at ambient temperature, cured in air at 130° C. for 20 minutes, soaked in 1.5% liquid detergent at ambient temperature for 15 minutes, rinsed thoroughly with water, and dried in air at 50° C. for 30 minutes. Then one-half of the swatches of each type were chlorinated by soaking them in 5% CLOROX at ambient temperature for 45 minutes. These chlorinated samples were rinsed thoroughly with water and dried in air at 50° C. for 30 minutes to remove all occluded free chlorine. Iodometric/thiosulfate titrations were performed on representative samples to determine initial chlorine loadings. The average chlorine loading for the silane monomer-coated samples was 0.61%; for the siloxane polymer-coated samples, the average chlorine loading was 0.40%. Then all types of coated swatches were subjected to laundry washing cycles using AATCC Test Method 61 (Test 2A Procedure). Samples were evaluated after 5, 10, and 50 washing cycles for retention of the coatings. Those samples not chlorinated before washing were chlorinated by the procedure described above in order to assess how much chlorine could be loaded after variable numbers of washing cycles. Those chlorinated before washing were divided into two groups with half being assessed for chlorine loading without rechlorination, the other half being rechlorinated and then assessed for chlorine loading. Three observations are clearly evident from the data in Table 3. First, both the silane and the siloxane coatings are partially lost upon successive washings. Second, prechlorination reduces the rate of loss, probably due to increasing the hydrophobicity of the surface, thus reducing the rate of hydrolysis loss of the siloxane coatings. Third, the siloxane coating, which is not chlorinated to as high a level as the silane one upon initial chlorination, is lost at a slower rate than is the silane coating. For all of the coatings, at least partial biocidal efficacy would be regenerated upon rechlorination after 50 washing cycles. Most probably, a low concentration of bleach added to washing cycles should maintain biocidal activity of the cotton material for the lifetime of the material.

Example 6

Alternative Preparation and Testing of a Representative Siloxane Compound

To a one-neck round-bottom flask were added 35 g of 3-triethoxysilylpropyl-5,5-dimethylhydantoin, prepared as described in Example 1, 18 mL of ethanol, 36 mL of water, and 0.25 to 0.5 mL of dilute hydrochloric acid (1:1 by volume) such that the final pH was in the range 3.5 to 5.5. The mixture was refluxed with stirring for 5 hours and then poured into an open beaker which was left in a vacuum oven at 60° C. for 3 hours, then 100° C. for 3 hours, then at 130° C. for 2 hours, and finally at 170° C. for 2 hours. The resulting glossy solid was a polymeric form of 3-trihydroxysilylpropyl-5,5-dimethylhydantoin. The material was not characterized other than by its performance as noted below.

The polymeric material prepared as described above was then used to coat the surfaces of military tenting, wood, glass, aluminum, and cotton. For the military tenting material, 2 g of the polymer were dissolved in 40 mL of ethanol to produce a 5% solution. Swatches of tenting material cut into 3-cm×4-cm rectangles were soaked in the polymer solution for 2 to 3 minutes and then dried at ambient temperature for 48 hours. Then the polymer coating was chlorinated by soaking the swatches in 10% CLOROX for 30 minutes at ambient temperature. Following rinsing and drying at ambient temperature, the chlorine loading on the surface of each swatch was determined using iodometric/thiosulfate titration. The loading averaged $4.2 \times 10^{16}$ Cl atoms per cm$^2$ after initial chlorination. Some of the swatches were reduced in thiosulfate and recharged. The average chlorine loading following the recharge was $5.3 \times 10^{16}$ Cl atoms per cm$^2$. The swatches were not tested for biocidal efficacy, but in our experience, any surface containing a chlorine loading of at least $1 \times 10^{16}$ atoms per cm$^2$ will be biocidal.

The same polymeric material was then coated onto wood (Tulip Poplar). In this case a 2.8% solution of the polymer in ethanol was used. Blocks of the wood having dimensions 5 cm×3.8 cm×1.9 cm were coated with the polymer solution using a cotton swab. The blocks were dried in air and then cured at 120° C. for 1 hour. Then chlorination was performed by soaking in 10% CLOROX for 30 minutes at ambient temperature. Following thorough rinsing with water and drying in air, an iodometric/thiosulfate titration indicated that the average chlorine loading was $1.57 \times 10^{17}$ Cl atoms per cm$^2$, which should give excellent biocidal efficacy. Analogous treatment of glass (FISHER microscope slides) and aluminum (REYNOLDS Heavy Duty Foil) gave chlorine loadings averaging $1.32 \times 10^{17}$ Cl atoms per cm$^2$ and $1.15 \times 10^{17}$ Cl atoms per cm$^2$, respectively.

Also, a solution containing 2.5 g of the polymer in 100 mL of ethanol (2.5%) was sloshed in a plastic (PET) bottle and then poured out. The solution was allowed to dry on the inside surface of the bottle, then cured for 1 hour at 65° C. Then the bottle was filled with 10% CLOROX for 30 minutes at ambient temperature. Following thorough rinsing with water and drying in air, a iodometric/thiosulfate titration indicated that the average chlorine loading was $5.3 \times 10^{16}$ Cl atoms per cm$^2$.

Finally, 100% cotton fabric swatches were tested. In this case 10 mL of the refluxed solution of polymer (the solid was not isolated) were mixed with 100 mL of a 50% ethanol/50% water solution in a beaker. The cotton swatches (7 g) were soaked in the solution for 3 minutes, then partially dried in air at ambient temperature, and then cured at 150° C. for 30 minutes. After soaking in 5% CLOROX for 20 minutes, the swatches were rinsed and dried at ambient temperature. The average chlorine loading of several swatches was determined by iodometric/thiosulfate titration to be 0.438% Cl. Then the other treated swatches were subjected to laundry washing cycles using AATCC Test Method 61 (Test 2A Procedure) followed by analytical determination of chlorine loading as a function of the number of wash cycles. After 5, 10, and 50 wash cycles the chlorine loadings averaged 0.282%, 0.279%, and 0.165%, respectively. A loading of even 0.165% Cl should exhibit reasonable biocidal efficacy.

Example 7

Preparation of and Coating with a Representative Silane Compound

The potassium salt of 2,2,5,5-tetramethylimidazolidin-4-one was prepared by refluxing a solution of 14.2 g (0.1 mol) of 2,2,5,5-tetramethylimidazolidin-4-one in 130 mL of xylene until all of the solid was dissolved. Then a solution of 5.6 g (0.1 mol) of potassium hydroxide in 6.46 mL of distilled, deionized water was added dropwise over a period of about 15 minutes, and the mixture was refluxed for an additional 2 hours until about 98% of the water produced in the reaction was removed. The solvent was removed under vacuum leaving the white solid potassium salt of 2,2,5,5-tetramethylimidazolidin-4-one. Then 100 mL of anhydrous DMF was added to the salt, and the mixture was heated to 100° C. until all solid was dissolved. Then 24.1 g (0.1 mol) of chloropropyltriethoxysilane were added dropwise to the mixture at 100° C. over a period of 45 minutes, and the mixture was held at 100° C. for an additional 12 hours. Then the mixture was filtered at ambient temperature to remove the potassium chloride produced in the reaction, and the DMF solvent was removed under vacuum. The crude product, 3-triethoxysilylpropyl-2,2,5,5-tetramethylimidazolidin-4-one (32.1 g; 92.6% crude yield), was a light brown viscous liquid which was used directly without further purification.

The crude product above was then coated onto cotton fabric. Swatches of cotton were soaked in a bath containing 8.0 g of the crude product, 45 mL of ethanol, and 45 mL of water for about 2 minutes, and then dried at ambient temperature in air. Then the swatches were cured at 100° C. for 45 minutes, soaked in 1.5% liquid detergent at ambient temperature for 15 minutes, rinsed thoroughly with water, and dried at 50° C. Chlorination was performed on the swatches using 5% CLOROX at ambient temperature for 45 minutes. Then the swatches were rinsed thoroughly with water and dried in air at 45° C. for 30 minutes. Iodometric/thiosulfate titration indicated an average chlorine loading of 0.114% for the cotton swatches. Although the initial chlorine loading of this coating on cotton is lower than that of the 3-triethoxysilylpropyl-5,5-dimethylhydantoin coating discussed in Example 4, its stability over time of storage and during washing is expected to be greater.

Example 8

Preparation of and Coating with a Representative Silane Compound

To 100 mL of ethanol in a 250 mL flask were added 76.6 g (0.4 mol) of dichloro-3-chloropropylmethylsilane (Gelest, Inc.) dropwise at ambient temperature over a period of 30 minutes. The mixture was then refluxed while stirring for 2 hours, and the excess ethanol was removed. The crude product (chloropropyldiethoxymethylsilane), 81.6 g, was obtained as a viscous oil in 96.9% yield. Then 33.2 g (0.2 mol) of the potassium salt of 5,5-dimethylhydantoin, prepared as described in Example 1, were mixed with 42.1 g (0.2 mol) of the chloropropyldiethoxymethylsilane in 150 mL of anhydrous DMF in a 500 mL flask, and the reaction mixture was held at 110° C. for 8 hours. The potassium chloride produced in the reaction was removed by filtration, and the DMF by vacuum distillation. The 3-diethoxymethylsilylpropyl-5,5-dimethylhydantoin product (56.47 g, 93.5% yield) was then used without further purification to coat cotton swatches. The swatches were soaked in a 10% solution of the 3-diethoxymethylsilylpropyl-5,5-dimethylhydantoin in 66.7% ethanol in water for 2.5 minutes at ambient temperature and then cured in air at 140° C. for 15 minutes. The treated swatches were then soaked in 1.5% liquid detergent at ambient temperature for 15 minutes, rinsed thoroughly with water, and dried in air at 50° C. for 30 minutes. The swatches were then chlorinated by soaking in 5% CLOROX at ambient temperature for 45 minutes, rinsed thoroughly with water, and dried in air at 50° C. to remove all occluded free chlorine. The chlorine loading was determined by iodometric/thiosulfate titration to be 0.733%. This magnitude of loading should give excellent biocidal performance. Furthermore, the increased hydrophobicity of the coating due to replacement of one ethoxy (hydroxy) group by the methyl alkyl group may render the surface more resistant to removal during washing than for the coating described in Example 5. Multi-washing cycles have not yet been performed for the coating described in this example.

Example 9

Preparation of and Coating with a Representative Silane Compound Containing an Amine Functional Group in the Linker To 11.06 g (0.05 mol) of 3-aminopropyltriethoxysilane in 75 mL of ethanol were added 9.52 g (0.05 mol) of 3-(2'-chloroethyl)-5,5-dimethylhydantoin. The mixture was refluxed for 5 hours, and then the ethanol solvent was removed under reduced pressure to give 18.10 g of a brown viscous oil (87.9% yield of 3-[2'-(3'-triethoxysilylpropyl)aminoethyl]-5,5-dimethylhydantoin hydrochloride which was used without further purification.

A bath containing 5.0 g of the crude product described above in 100 mL of a 50% ethanol/water solution was prepared. Cotton swatches were soaked in the bath for 30 minutes. The swatches were then cured at 95° C. for 1 hour, followed by soaking in 1.5% liquid detergent for 15 minutes, and rinsing thoroughly with water. After drying at 50° C., the swatches were chlorinated with a 5% solution of CLOROX for 5 minutes at ambient temperature. Following a thorough rinse with water, the swatches were held at 50° C. in air until dry and then further dried in air overnight at ambient temperature. The chlorine loading was determined to be 0.44% by iodometric/thiosulfate titration.

The crude product from above was also used to treat sand. Sand (Ottawa Sand Standard, 20–30 mesh, Fisher Chemicals) was stirred in a bath containing 5% of the crude product and 100 mL of a 50% ethanol/water solution for 30 minutes at ambient temperature. The treated sand was collected by filtration, cured at 95° C. in air for 1 hour, soaked in methanol for 10 minutes, rinsed with water, and then dried at 45° C. in air for 2 hours. The sand was then chlorinated by exposure to 50% CLOROX solution for 15 minutes. After thorough rinsing with water and drying at 50° C. in air for 2 hours, the chlorine loading was found to be 0.11% by iodometric/thiosulfate titration.

Example 10

Odor Control Properties of Non-woven Matrix Coated with a Representative Chlorinated Silane Compound 3-triethoxysilylpropyl-5,5-dimethylhydantoin, prepared as described in Example 1, was used to treat non-woven pads consisting of 1 gram of a wood pulp matrix such as is used in diapers and incontinence products. A 5% solution prepared in a distilled water and ethanol 1:1 mixture was applied to pads of the wood pulp fibers, and they were then left to soak for 5 minutes. Excess solution was vacuum suctioned from the pads, which were then dried in an oven at 90° C. for two hours. Untreated pads were also subjected to exposure to water and ethanol as controls, and were similarly dried.

Dried coated test samples and uncoated control pads were then treated by exposure to 10% sodium hypochlorite solution for 15 minutes, after which they were rinsed exhaustively with distilled water, and then vacuum dried to remove any unbound, free chlorine. Additional control pads consisted of wood pulp coated with 3-triethoxysilylpropyl-5,5-dimethylhydantoin but not exposed to the hypochlorite bleach charge. These were rinsed thoroughly along with the test articles, and dried under the same conditions. All dried pads were then left for 48 hours on the bench of a laboratory fume hood before being used in the experiments.

All test and control pads were then exposed to an inoculum designed to generate ammonia odor as a result of bacterial action on urine, simulating events in an infant or adult human diaper. Each inoculum consisted of 1 mL of pooled human female urine, supplemented with 50 mg of urea, mixed with 0.1 mL of a culture of *Proteus mirabilis* bacteria, and spread evenly over the surface of the pad. All pads were then kept at 37° C. for six hours in individual containers sealed with parafilm. At the end of this period the samples were removed from the incubator, and the amount of ammonia gas in the head space above each pad was measured as an indicator of the degree of odor generated in the urine. Ammonia measurements were made using a Drager gas sampling device.

All control samples at the end of the incubation showed more than 30 ppm of ammonia present in the head space above the pads. In the case of the pads coated with 3-triethoxysilylpropyl-5,5-dimethylhydantoin and halogenated with chlorine, the samples showed no detectable ammonia (lower limit of detection, 0.25 ppm). Control samples had a powerful odor of ammonia, readily detected by the human nose, whereas the samples above the treated test pads had no detectable odor whatsoever.

The results in this example show that halogenated 3-triethoxysilylpropyl-5,5-dimethylhydantoin can coat wood pulp fibers, and that this coating is highly effective in inhibiting microbial production of odor by suspensions of bacteria in human urine. Moreover, once applied to the fibers, this antimicrobial coating is not readily removed by extensive washing, and subsequent drying. Coated nonwoven matrices of wood pulp (cellulose) and other fibers should be excellent as components of diapers and incontinence pad devices which will resist the development of odors during normal use.

Example 11

Antiviral Properties of Surfaces Coated with Representative a Chlorinated Silane Compound Soft and hard surfaces were treated by exposure to a solution of 3-triethoxysilylpropyl-5,5-dimethylhydantoin, as prepared in Example 1, and then halogenated with hypochlorite bleach, prior to being exposed to a challenge inoculum of a virus (MS2 phage). After passage of measured contact times, recovery of viable infective virus particles was attempted from treated and control surfaces in order to demonstrate the inactivating efficacy of the halogenated surfaces. Soft surfaces used in these experiments were swatches of woven cotton textiles, and slabs cut from a standard kitchen sponge. Hard surfaces used were porcelain and marble tiles.

For the preparation of antimicrobial textiles, fabric and sponge samples were immersed in 5% solution of 3-triethoxysilylpropyl-5,5-dimethylhydantoin and dried in a convection oven at 90° C. for two hours. Chlorination of the coated cellulose materials was accomplished by placing them in the wash chamber of a standard, household washing machine, and processing them through a normal, cold water small load cycle, with one rinse. The washing solution contained 100 mL of CLOROX ULTRA (sodium hypochlorite) per load. This procedure was used to simulate an everyday process that could be used by the consumer to charge coated fibers of treated textiles in a home environment. Drying of each load was done in a domestic dryer for 30 minutes at medium heat setting. Successful chlorination of laundered textiles was confirmed by iodometric/thiosulfate titration of the bound chlorine on swatches of each test material. Uncoated, normal fabric was used as a control in these experiments. Chlorine contents were calculated and expressed as ppm $Cl^+$. These values for cotton were approximately 4000, and for the sponge slabs 1000–2000 ppm, Hard surface samples were exposed to the 3-triethoxysilylpropyl-5,5-dimethylhydantoin by using a sponge soaked in the 5% solution, before transfer to a drying oven at 90° C. for two hours. Alternatively, test tiles were immersed in the 5% solution, before drying. Chlorination of hard surfaces was accomplished by sponging on a 10% solution of CLOROX bleach and allowing the samples to stand for up to 20 minutes at room temperature before rinsing exhaustively with distilled water, and allowing them to dry at room temperature. Uncoated tiles were used as controls; they were exposed to hypochlorite before rinsing and drying. In addition, coated surfaces that remained uncharged with chlorine were used as controls in challenge inocula experiments. Chlorine bound to hard surfaces was determined by iodometric/thiosulfate titration, and chlorine contents were expressed as $\mu g$ $Cl^+$ per square cm. These values were 3.3 for the porcelain, and 6.9 for the marble tile.

Challenge inocula for determination of antiviral activity of halogenated coatings were made with suspensions of MS2 virus harvested from lawns of *Escherichia coli* bacterial host cells on trypticase soy agar (TSA) plates using standard methods. The test protocol used was a slightly modified version of Method 100-1998 from the American Association of Textile Chemists and Colorists (AATCC). One mL aliquots of a stock suspension of virus of known titer were applied to swatches of the textiles, 5 cm in diameter, for defined contact times (ct) at room temperature. The swatches were then treated with 0.02 M sodium thiosulphate solution to neutralize any remaining active chlorine, and agitated in phosphate buffered water for recovery of infective virus particles. Enumeration of recovered organisms was accomplished by plating dilutions of the recovery solution onto *E. coli* lawns on TSA. Each infective virus particle recovered in this assay gives rise to a plaque of lysed host cells after 24 hours of incubation at 37° C. By enumeration of visible plaques on the surface of the agar plates, the proportion of the challenge inocula remaining after contact with the swatches was determined. The results are expressed as Log 10 reductions in the test samples when compared to the recovery from untreated control swatches.

Inoculation of hard surfaces was done using a protocol which was similar in principle. It was modified to allow for the retention of the challenge inocula in contact with the hard test surface during the entire incubation period. This was accomplished by creating a "sandwich" of the inoculum suspension between a glass microscope cover slip and the test article. By this means, losses of the inocula by evaporation were avoided, and the exact surface area in contact with the challenge organisms was readily calculated. Recovery of infective virus particles was again achieved by agitation in recovery solution containing thiosulphate neutralizer, and the results again expressed as reductions in Log 10 titer of the MS2 virus compared to the controls.

Results showed that cellulose textile and sponge samples coated with chlorinated 3-triethoxysilylpropyl-5,5-dimethylhydantoin showed a remarkable capacity to inactivate the tough viral particles of MS2 phage. Reductions of approximately 4 logs were consistently achieved with cellulose substrates after 24 hours of contact. On hard surfaces titers were reduced by approximately 2 logs after contact times of as little as 6 hours. Small non-enveloped viral particles are particularly durable in the environment and generally not highly susceptible to chemical deactivation. These data therefore indicate that antimicrobial surfaces created with halogenated 3-triethoxysilylpropyl-5,5-dimethylhydantoin will have demonstrable antiviral functions when used as a means of protecting environmental surfaces against persistent contamination by viruses.

Example 12

Antifungal Properties of Surfaces Coated with a Representative Chlorinated Silane Compound Soft and hard surfaces were treated by exposure to a solution of 3-triethoxysilylpropyl-5,5-dimethylhydantoin, prepared as described in Example 1. The soft surfaces used for detection of antifungal properties were woven textiles composed of fibers of polypropylene, cotton (cellulose), polyester, rayon, and slabs from a cellulose kitchen sponge. Hard surfaces prepared were polyvinylchloride (PVC) sheets, and porcelain and marble tiles. Challenge inocula of prepared surfaces consisted of aliquots of stock suspensions of spores of *Aspergillus niger* (ATCC # 1004), a black mold, harvested from cultured lawns on Potato Dextrose Agar (PDA) plates. Methods for preparation of the halogen charged surfaces and protocols for challenge were as described in Example 11. In this case recovery of *Aspergillus* was accomplished by the plate dilution method on PDA, and the results were expressed as log 10 reductions compared to the controls. Contact times varied from 24–72 hours, considerably longer than was allowed for other organisms because of the well established durability of black mold spores under a wide range of physical and chemical conditions.

Chlorine concentrations on the tested soft surfaces ranged from approximately 800 on the synthetic fibers up to 4000 ppm on rayon fabrics. Hard surfaces were shown to range from 4.1 $\mu g$ per $cm^2$ for the PVC, up to 6.9 $\mu g$ per $cm^2$ for the marble tiles. All of the soft and hard surfaces tested showed activity against *Aspergillus* black mold. After contact times of 24 hours on cotton, reductions of 8 logs were observed in mold concentrations, with a 4 log reduction recorded for the sponge slabs. On synthetic fibers reductions of 5 logs (polypropylene, polyester) were observed after 72 hours of contact. On hard surfaces the corresponding log reductions at 72 hours after spore inoculation were 4 (marble), 5 (porcelain), and 4 (vinyl).

These data indicate that effective control of spores of molds can be expected from the use of halogenated coatings of 3-triethoxysilylpropyl-5,5-dimethylhydantoin on a variety of soft and hard substrates. It is likely that the disadvantages of odor and black discoloration associated with mold growth can be avoided by use of these coatings, and their periodic recharge by exposure to free halogen in bleach.

Example 13

Anti-yeast Properties of Surfaces Coated with a Representative Halogenated Silane Soft and hard surfaces were treated by exposure to solutions of 3-triethoxysilylpropyl-5,5-dimethylhydantoin prepared as described in Example 1. Challenge inocula for determination of activity directed against yeasts consisted of suspensions of Candida albicans (ATCC # 102301) harvested from PDA plates. Procedures for preparation of halogen charged surfaces, plates, and the exposure of test articles were as described in Example 11. Recovery of viable Candida was accomplished by the plate dilution method on PDA.

All halogen charged surfaces expressed activity against inocula of yeast organisms in this test. Reductions in viable yeasts in plate counts were rapid on cotton surfaces (5 logs in two hours of contact), but took longer on synthetic textiles (4 logs in 24 hours on polyester). On hard surfaces reductions of up to 4 logs took place in 6 hours of contact.

These results indicate that antimicrobial coatings consisting of halogenated 3-triethoxysilylpropyl-5,5-dimethylhydantoin can be expected to exert powerful anti-yeast activities on soft and hard surfaces. Yeasts, such as Candida, are known to cause dermal irritation in diapers, to cause severe odors, and to colonize and persist on many surfaces in biofilm slime layers. Products containing these compounds may therefore be useful in reducing the clinical and nuisance significance of yeast microbes.

Example 14

Anti Bacillus (Bacterial) Spore Activity of Surfaces Coated with a Representative Halogenated Silane Compound Soft and hard surfaces were treated by exposure to solutions of 3-triethoxysilylpropyl-5,5-dimethylhydantoin, prepared as described in Example 1, and charged with chlorine as described in Example 11. Challenge inocula for the detection of activity versus bacterial spores were prepared from suspensions of spores of Bacillus subtilis. Recovery of viable organisms from challenged surfaces was done on TSA plates, and enumeration was accomplished by the plate dilution method.

The most significant reductions in viable B. subtilis spore counts on textile substrates were obtained after prolonged exposures on cotton and on polyester (>2 logs in 96 hours), while spores in contact with cellulose sponge were depleted by >5 logs in the same contact period. On hard surfaces reductions up to 4 logs were seen on marble, vinyl, and porcelain when contact times were extended to 96 hours.

These results indicate that chlorine-charged antimicrobial surfaces prepared with 3-triethoxysilylpropyl-5,5-dimethylhydantoin coatings are effective even on the most resistant stages of bacteria, the spores of anaerobic organisms, provided sufficiently long contact is allowed. This may be useful in the killing of spores trapped in non-woven matrix air filters, for example, or in the matrix used for filtration of other protective devices, in air duct surfaces, and in other situations where occupational exposure of workers to such organisms is a hazard, or in the circumstances where deliberate distribution of such spores may be introduced in acts of biological warfare or bioterrorism.

Example 15

Chlorine Binding by a Representative Silane Compound on Hard and Soft Surfaces

A variety of surfaces were coated with the 3-triethoxysilylpropyl-5,5-dimethylhydantoin monomer, prepared as described in Example 1, then cured at various temperatures, and chlorinated with dilute solutions of CLOROX using similar procedures to those discussed in previous examples. The surfaces were then evaluated for their efficacies in loading chlorine either quantitatively by iodometric/thiosulfate titration or qualitatively by colorimetric visualization of exposure of the surfaces to potassium iodide and starch solution. The soft materials bound chlorine in the range of 500 to 5000 ppm expressed as $Cl^+$, while the hard surfaces bound it in the range of $5.8 \times 10^{16}$ to $2.5 \times 10^{17}$ Cl atoms per $cm^2$.

The following materials showed efficacy in chlorine binding in the study: glass, sand, ceramics, nylon, acrylonitrile, latex rubber, polyvinylchloride laminates, polyester, polyurethane, TYVEK, silica gel, chitosan, chitin, Formica, unglazed porcelain, glazed porcelain, aluminum, silicon tubing, clear acrylic films, steel, cement grout, and latex caulk. In fact, no material tested failed to bind chlorine after treatment.

This example demonstrates a great versatility of chlorine binding to surfaces treated with the 3-triethoxysilylpropyl-5,5-dimethylhydantoin monomer. The other silane monomers and siloxane polymers which are the subjects of this invention should behave in similar fashion, and if a loading of at least $1 \times 10^{16}$ atoms of Cl per $cm^2$ can be obtained, the surfaces will then exhibit biocidal activity.

Example 16

Antimicrobial Activity of Textile Surfaces Coated with a Representative Acyclic Silane Compound Cotton textiles were coated with 3-aminopropyltriethoxysilane by exposure to aqueous solutions of 5% of this compound, followed by curing the woven fabric at 100° C. for 60 minutes in air, or by use of a household dryer on high setting for 30 minutes. Swatches of the treated fabric were charged with chlorine, and then challenged with suspensions of Staphylococcus aureus; enumeration of recovery was accomplished using the methods described in Example 11. Chlorine contents of charged oven-cured textiles ranged up to 5000 ppm (5 mg per g of material) immediately after drying, but diminished to 2300 ppm in approximately 14 days at 20° C. Chlorine concentrations in dryer-prepared swatches were never higher than 2500 ppm, even when fresh. Reductions of viable organisms in freshly chlorinated oven-dried swatches were in excess of 4 logs, after as little as 15 minutes of contact. Longer contact times (30 minutes) were required to reach this level of efficacy in dryer-cured textiles.

These results indicate that acyclic siloxanes can bind to cellulose textiles, and when charged with chlorine, can exhibit potent antimicrobial effects, but with less durability than with the cyclic N-halamine series. As a general rule, N—Cl or N—Br bonds are always stronger when in cyclic molecules than they are in their acyclic analogs. Nevertheless, these properties may find utility in the preparation of biocidal textiles that are subject to frequent recharge cycles such as clothing and certain cleaning tools, such as mops and cloths.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A compound having the structure

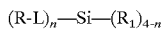

wherein R1 is independently selected from a C1–C4 alkyl, aryl, C1–C4 alkoxy, hydroxy, chloro, or C1–C4 ester group, wherein at least one R1 group is a C1–C4 alkoxy, hydroxy, chloro, or C1–C4 ester group; wherein L is a linker group; wherein n=1, 2, or 3; and wherein R is a heterocyclic N-halamine.

2. The compound of claim 1, wherein L is a linker alkylene, amine, or ether group, comprised of 1–13 carbons, 0–3 nitrogen or oxygen atoms, of L is a linker alkylene group of 1–13 carbons and a carbonate, thiocarbanote, or urea functional group.

3. A compound having the structure

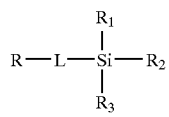

wherein R1, R2, and R3 are independently selected from a C1–C4 alkyl, aryl, C1–C4 alkoxy, hydroxy, chloro, or C1–C4 ester group, wherein at least one of R1, R2, or R3 is a C1–C4 alkoxy, hydroxy, chloro, or C1–C4 ester group; wherein L is a linker group; and wherein R is a heterocyclic N-halamine.

4. A compound having the structure

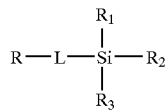

wherein R1, R2, and R3 are independently selected from a C1–C4 alkyl, aryl, C1–C4 alkoxy, hydroxy, chloro, or C1–C4 ester group, wherein at least one of R1, R2, or R3 is a C1–C4 alkoxy, hydroxy, chloro, or C1–C4 ester group; wherein L is a linker group; and wherein R is a heterocyclic N-halamine having the structure

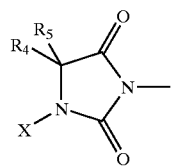

wherein R4 and R5 are independently selected from a C1–C4 alkyl, aryl, or hydroxymethyl group; and wherein X is at least one of chlorine or bromine.

5. The compound of claim 4, wherein R1, R2, R3 are independently selected from a methyl, ethyl, phenyl, methoxy, ethoxy, or hydroxy group; wherein at least one of R1, R2, or R3 is a methoxy, ethoxy, or hydroxy group; and wherein R4 and R5 are independently selected from a methyl, ethyl, hydroxymethyl or phenyl group.

6. The compound of claim 5, wherein R1, R2, and R3 are a methoxy or ethoxy group; R4 and R5 are a methyl group, and L is a linker alkylene, amine, or ether group, comprised of 1–7 carbons and 0–1 nitrogen or oxygen atoms, or L is a linker alkylene group, comprised of 1–7 carbons and a carbamate, thiocarbamate, or urea functional group.

7. The compound of claim 6, wherein R1, R2, R3 are a methoxy group; X is chlorine; and L is a linker alkylene comprised of 3 carbons.

8. The compound of claim 6, wherein R1, R2, R3 are a methoxy group; X is bromine; and L is a linker alkylene comprised of 3 carbons.

9. The compound of claim 6, wherein R1, R2, and R3 are an ethoxy group; X is chlorine; and L is a linker alkylene comprised of 3 carbons.

10. The compound of claim 6, wherein R1, R2, and R3 are an ethoxy group; X is bromine; and L is a linker alkylene comprised of 3 carbons.

11. The compound of claim 6, wherein R1, R2, and R3 are a methoxy group; X is chlorine; and L is a linker amine or ether group comprised of 4 carbons, and 1 nitrogen or oxygen atom.

12. The compound of claim 6, wherein R1, R2, and R3 are a methoxy group; X is bromine; and L is a linker amine or ether group comprised of 4 carbons, and 1 nitrogen or oxygen atom.

13. The compound of claim 6, wherein R1, R2, and R3 are an ethoxy group; X is chlorine; and L is a linker amine or ether group comprised of 4 carbons, and 1 nitrogen or oxygen atom.

14. The compound of claim 6, wherein R1, R2, and R3 are an ethoxy group; X is bromine; and L is a linker amine or ether group comprised of 4 carbons, and 1 nitrogen or oxygen atom.

15. The compound of claim 6, wherein R1, R2, and R3 are a methoxy group; X is chlorine; and L is a linker alkylene group comprised of 4 carbons and a carbamate, thiocarbamate, or urea functional group.

16. The compound of claim 6, wherein R1, R2, and R3 are a methoxy group; X is bromine; and L is a linker alkylene group comprised of 4 carbons and a carbamate, thiocarbamate, or urea functional group.

17. The compound of claim 6, wherein R1, R2, and R3 are an ethoxy group; X is chlorine; and L is a linker alkylene group comprised of 4 carbons and a carbamate, thiocarbamate, or urea functional group.

18. The compound of claim 6, wherein R1, R2, and R3 are an ethoxy group; X is bromine; and L is a linker alkylene group comprised of 4 carbons and a carbamate, thiocarbamate, or urea functional group.

19. A compound having the structure

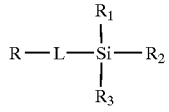

wherein R1, R2, and R3 are independently selected from a C1–C4 alkyl, aryl, C1–C4 alkoxy, hydroxy, chloro, or C1–C4 ester group, wherein at least one of R1, R2, or R3 is a C1–C4 alkoxy, hydroxy, chloro, or C1–C4 ester group; wherein L is a linker group; and wherein R is a heterocyclic amine having the structure

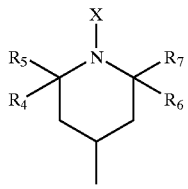

wherein R4, R5, R6, and R7 are independently selected from a C1–C4 alkyl, aryl, or hydroxymethyl group; and wherein X is chlorine or bromine.

20. The compound of claim 19, wherein R1, R2, and R3 are a methoxy, ethoxy, or hydroxy group; R4, R5, R6, and R7 are a methyl group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbomate, or urea functional group.

21. A compound having the structure

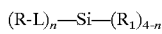

(R-L)$_n$—Si—(R$_1$)$_{4-n}$ wherein R1 is independently selected from a C1–C4 alkyl, aryl, C1–C4 alkoxy, hydroxy, chloro, or C1–C4 ester group, wherein at least one R1 group is a C1–C4 alkoxy, hydroxy, chloro, or C1–C4 ester group; wherein L is a linker group; wherein n=1, 2, or 3; and wherein R is a heterocyclic N-halamine from at least one of a hydantoin, imidazolidinone, oxazolidinone, isocyanurate, glycoluril, and triazinedione.

22. A compound having the structure

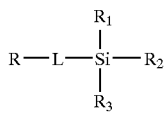

wherein R1, R2, and R3 are independently selected from a C1–C4 alkyl, aryl, C1–C4 alkoxy, hydroxy, chloro, or C1–C4 ester group, wherein at least one of R1, R2, or R3 is a C1–C4 alkoxy, hydroxy, chloro, or C1–C4 ester group; wherein L is a linker group; and wherein R is a heterocyclic N-halamine from at least one of a hydantoin, imidazolidinone, oxazolidinone, isocyanurate, glycoluril, and triazinedione.

23. A compound having the structure

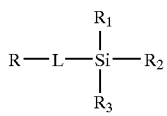

wherein R1, R2, and R3 are independently selected from a C1–C4 alkyl, aryl, C1–C4 alkoxy, hydroxy, chloro, or C1–C4 ester group, wherein at least one of R1, R2, or R3 is a C1–C4 alkoxy, hydroxy, chloro, or C1–C4 ester group; wherein L is a linker group; and wherein R is a heterocyclic amine having the structure

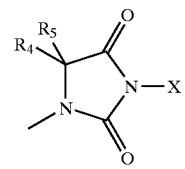

wherein R4 and R5 are independently selected from a C1–C4 alkyl, aryl, or hydroxymethyl group; and wherein X is at least one of chlorine or bromine.

24. A compound having the structure

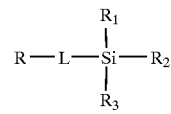

wherein R1, R2, and R3 are independently selected from a C1–C4 alkyl, aryl, C1–C4 alkoxy, hydroxy, chloro, or C1–C4 ester group, wherein at least one of R1, R2, or R3 is a C1–C4 alkoxy, hydroxy, chloro, or C1–C4 ester group; wherein L is a linker group; and wherein R is a heterocyclic amine having the structure

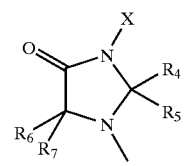

wherein R4, R5, R6, and R7 are independently selected from a C1–C4 alkyl, aryl, or hydroxymethyl group; and wherein X is at least one of chlorine, or bromine.

25. The compound of claim 24, wherein R1, R2, and R3 are a methoxy, ethoxy, or hydroxy group; R4, R5, R6, and R7 are a methyl group; and L is a linker alkylene, amine, or ether group, comprised of 1–4 carbons, and 0–1 nitrogen or oxygen atoms, or L is a linker alkylene group, comprised of 1–4 carbons, and a carbamate, thiocarbamate, or urea functional group.

26. A compound having the structure

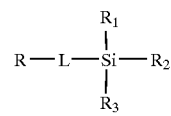

wherein R1, R2, and R3 are independently selected from a C1–C4 alkyl, aryl, C1–C4 alkoxy, hydroxy, chloro, or C1–C4 ester group, wherein at least one of R1, R2, or R3 is a C1–C4 alkoxy, hydroxy, chloro, or C1–C4 ester group; wherein L is a linker group; and wherein R is a heterocyclic amine having the structure

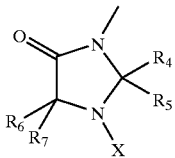

wherein R4, R5, R6, and R7 are independently selected from a C1–C4 alkyl, aryl, or hydroxymethyl group; and wherein X is at least one of chlorine, or bromine.

27. A compound having the structure

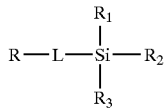

wherein R1, R2, and R3 are independently selected from a C1–C4 alkyl, aryl, C1–C4 alkoxy, hydroxy, chloro, or C1–C4 ester group, wherein at least one of R1, R2, or R3 is a C1–C4 alkoxy, hydroxy, chloro, or C1–C4 ester group; wherein L is a linker group; and wherein R is a heterocyclic amine having the structure

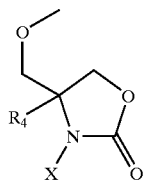

wherein R4 is at least one of a C1–C4 alkyl, aryl, or hydroxymethyl group; and wherein X is at least one of chlorine, or bromine.

28. The compound of claim 27, wherein R1, R2, and R3 are a methoxy, ethoxy, or hydroxy group; R4 is a methyl, ethyl, or hydroxymethyl group; and L is a linker alkylene group, comprised of 1–3 carbons, or L is a linker alkylene group, comprised of 1–3 carbons, and a carbamate, thiocarbomate, or urea functional group.

29. A compound having the structure

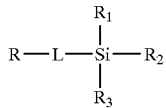

wherein R1, R2, and R3 are independently selected from a C1–C4 alkyl, aryl, C1–C4 alkoxy, hydroxy, chloro, or C1–C4 ester group, wherein at least one of R1, R2, or R3 is a C1–C4 alkoxy, hydroxy, chloro, or C1–C4 ester group; wherein L is a linker group; and wherein R is a heterocyclic amine having the structure

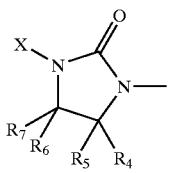

wherein R4, R5, R6, and R7 are independently selected from a C1–C4 alkyl, aryl, or hydroxymethyl group; and wherein X is at least one of chlorine, or bromine.

30. The compound of claim 29, wherein R1, R2, and R3 are a methoxy, ethoxy or hydroxy group; R4, R5, R6, and R7 are a methyl group; and L is a linker alkylene, amine, or ether group, comprised of 1–4 carbons, and 0–1 nitrogen or oxygen atoms, or L is a linker alkylene group, comprised of 1–4 carbons, and a carbamate, thiocarbamate, or urea functional group.

31. A compound having the structure

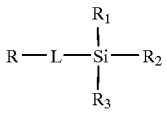

wherein R1, R2, and R3 are independently selected from a C1–C4 alkyl, aryl, C1–C4 alkoxy, hydroxy, chloro, or C1–C4 ester group, wherein at least one of R1, R2, or R3 is a C1–C4 alkoxy, hydroxy, chloro, or C1–C4 ester group; wherein L is a linker group; and wherein R is a heterocyclic amine having the structure

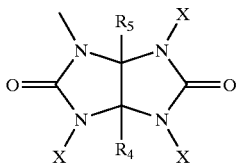

wherein R4 and R5 are independently selected from a C1–C4 alkyl, aryl, or hydroxymethyl group; and wherein X is independently selected from at least one of hydrogen, chlorine, bromine, or hydroxymethyl; and wherein at least one X is chlorine, or bromine.

32. The compound of claim 31, wherein R1, R2, and R3 are a methoxy, ethoxy, or hydroxy group; R4 and R5 are a methyl group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbomate, or urea functional group.

33. A compound having the structure

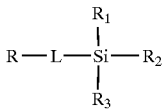

wherein R1, R2, and R3 are independently selected from a C1–C4 alkyl, aryl, C1–C4 alkoxy, hydroxy, chloro, or C1–C4 ester group, wherein at least one of R1, R2, or R3 is a C1–C4 alkoxy, hydroxy, chloro, or C1–C4 ester group; wherein L is a linker group; and wherein R is a heterocyclic amine having either structure

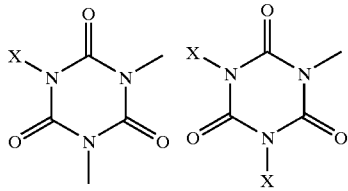

wherein X is independently selected from at least one of hydrogen, chlorine, bromine, or hydroxymethyl; and wherein at least one X is chlorine, or bromine.

34. The compound of claim 33, wherein R1, R2, and R3 are a methoxy, ethoxy, or hydroxy group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbomate, or urea functional group.

35. A compound having the structure

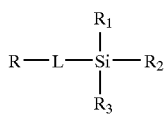

wherein R1, R2, and R3 are independently selected from a C1–C4 alkyl, aryl, C1–C4 alkoxy, hydroxy, chloro, or C1–C4 ester group, wherein at least one of R1, R2, or R3 is a C1–C4 alkoxy, hydroxy, chloro, or C1–C4 ester group; wherein L is a linker group; and wherein R is a heterocyclic amine having the structure

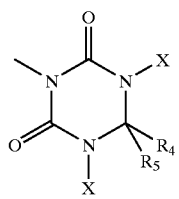

wherein R4 and R5 are independently selected from a C1–C4 alkyl, aryl, or hydroxymethyl group; and wherein X is independently selected from at least one of hydrogen, chlorine, bromine, or hydroxymethyl; and wherein at least one X is chlorine, or bromine.

36. The compound of claim 35, wherein R1, R2, and R3 are a methoxy, ethoxy, or hydroxy group; R4 and R5 are a methyl group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbomate, or urea functional group.

37. A compound having the structure

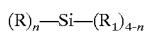

wherein R1 is independently selected from a C1–C4 alkyl, aryl, C1–C4 alkoxy, hydroxy, chloro, or C1–C4 ester group, wherein at least one R1 group is a C1–C4 alkoxy, hydroxy, chloro, or C1–C4 ester group; wherein n=1, 2, or 3; and wherein R is an amino alkylene or polyamino alkylene group comprising at least one of an N-chloro or an N-bromo group.

38. A compound having the structure

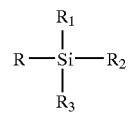

wherein R1, R2, and R3 are independently selected from a C1–C4 alkyl, aryl, C1–C4 alkoxy, hydroxy, chloro, or C1–C4 ester group, wherein at least one of R1, R2, or R3 is a C1–C4 alkoxy, hydroxy, chloro, or C1–C4 ester group; and wherein R is an amino alkylene or polyamino alkylene group comprising at least one of an N-chloro or an N-bromo group.

39. The compound of claim 38, wherein R is an amino propyl group.

40. A siloxane, comprising the structure

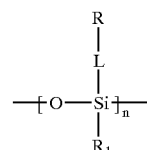

wherein, $n \geq 2$; R1 is at least one of a C1–C4 alkyl, aryl, C1–C4 alkoxy, hydroxy, chloro, or C1–C4 ester group; wherein L is a linker group; and wherein R is a heterocyclic N-halamine.

41. A siloxane, comprising the structure

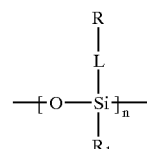

wherein, $n \geq 2$; R1 is at least one of a C1–C4 alkyl, aryl, C1–C4 alkoxy, hydroxy, chloro, or C1–C4 ester group; wherein L is a linker group; and wherein R is a heterocyclic amine having the structure

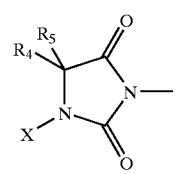

wherein R4 and R5 are independently selected from a C1–C4 alkyl, aryl, or hydroxymethyl group; and wherein X is at least one of chlorine or bromine.

42. A siloxane, comprising the structure

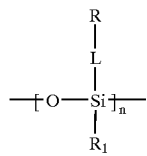

wherein, n≧2; R1 is at least one of a C1–C4 alkyl, aryl, C1–C4 alkoxy, hydroxy, chloro, or C1–C4 ester group; wherein L is a linker group; and wherein R is a heterocyclic N-halamine from at least one of an hydantoin, imidazolidinone, oxazolidinone, isocyanurate, glycoluril, triazinedione, and piperidine.

43. A siloxane, comprising the structure

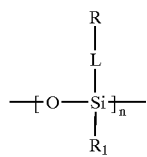

wherein, n≧2; R1 is at least one of a C1–C4 alkyl, aryl, C1–C4 alkoxy, hydroxy, chloro, or C1–C4 ester group; wherein L is a linker group; and wherein R is a heterocyclic amine having the structure

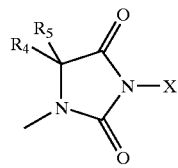

wherein R4 and R5 are independently selected from a C1–C4 alkyl, aryl, or hydroxymethyl group; and wherein X is at least one of chlorine or bromine.

44. A siloxane, comprising the structure

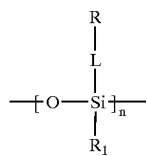

wherein, n≧2; R1 is at least one of a C1–C4 alkyl, aryl, C1–C4 alkoxy, hydroxy, chloro, or C1–C4 ester group; wherein L is a linker group; and wherein R is a heterocyclic amine having the structure

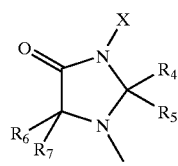

wherein R4, R5, R6, and R7 are independently selected from a C1–C4 alkyl, aryl, or hydroxymethyl group; and wherein X is at least one of chlorine or bromine.

45. A siloxane, comprising the structure

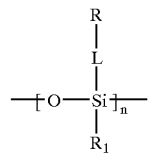

wherein, n≧2; R1 is at least one of a C1–C4 alkyl, aryl, C1–C4 alkoxy, hydroxy, chloro, or C1–C4 ester group; wherein L is a linker group; and wherein R is a heterocyclic amine having the structure

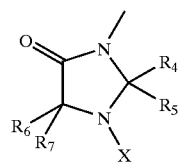

wherein R4, R5, R6, and R7 are independently selected from a C1–C4 alkyl, aryl, or hydroxymethyl group; and wherein X is at least one of chlorine or bromine.

46. A siloxane, comprising the structure

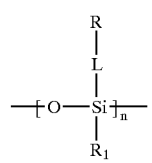

wherein, n≧2; R1 is at least one of a C1–C4 alkyl, aryl, C1–C4 alkoxy, hydroxy, chloro, or C1–C4 ester group; wherein L is a linker group; and wherein R is a heterocyclic amine having the structure

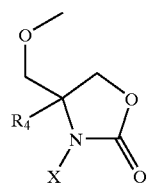

wherein R4 is at least one of a C1–C4 alkyl, aryl, or hydroxymethyl group; and wherein X is at least one of chlorine or bromine.

47. A siloxane, comprising the structure

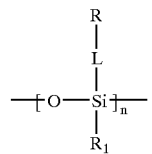

wherein, n≧2; R1 is at least one of a C1–C4 alkyl, aryl, C1–C4 alkoxy, hydroxy, chloro, or C1–C4 ester group;

wherein L is a linker group; and wherein R is a heterocyclic amine having the structure

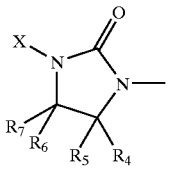

wherein R4, R5, R6, and R7 are independently selected from a C1–C4 alkyl, aryl, or hydroxymethyl group; and wherein X is at least one of chlorine or bromine

48. A siloxane, comprising the structure

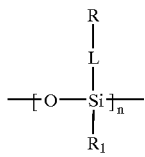

wherein, $n \geq 2$; R1 is at least one of a C1–C4 alkyl, aryl, C1–C4 alkoxy, hydroxy, chloro, or C1–C4 ester group; wherein L is a linker group; and wherein R is a heterocyclic amine having the structure

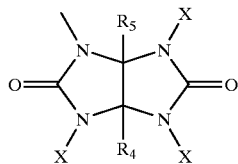

wherein R4 and R5 are independently selected from a C1–C4 alkyl, aryl, or hydroxymethyl group; wherein X is independently selected from at least one of hydrogen, chlorine, bromine, or hydroxymethyl; and wherein at least one X is chlorine or bromine.

49. A siloxane, comprising the structure

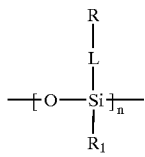

wherein, $n \geq 2$; R1 is at least one of a C1–C4 alkyl, aryl, C1–C4 alkoxy, hydroxy, chloro, or C1–C4 ester group; wherein L is a linker group; and wherein R is a heterocyclic amine having either structure

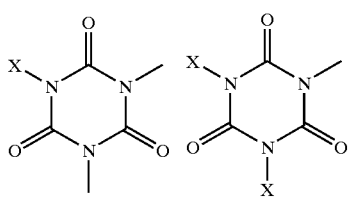

wherein X is independently selected from at least one of hydrogen, chlorine, bromine, or hydroxymethyl; and wherein at least one X is chlorine or bromine.

50. A siloxane, comprising the structure

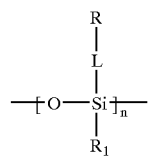

wherein, $n \geq 2$; R1 is at least one of a C1–C4 alkyl, aryl, C1–C4 alkoxy, hydroxy, chloro, or C1–C4 ester group; wherein L is a linker group; and wherein R is a heterocyclic amine having the structure

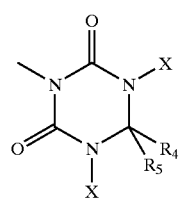

wherein R4 and R5 are independently selected from a C1–C4 alkyl, aryl, or hydroxymethyl group; wherein X is independently selected from at least one of hydrogen, chlorine, bromine, or hydroxymethyl; and wherein at least one X is chlorine or bromine.

51. A siloxane, comprising the structure

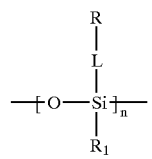

wherein, $n \geq 2$; R1 is at least one of a C1–C4 alkyl, aryl, C1–C4 alkoxy, hydroxy, chloro, or C1–C4 ester group; wherein L is a linker group; and wherein R is a heterocyclic amine having the structure

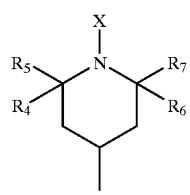

wherein R4, R5, R6, and R7 are independently selected from a C1–C4 alkyl, aryl, or hydroxymethyl group; and wherein X is at least one of chlorine or bromine

52. A siloxane, comprising the structure

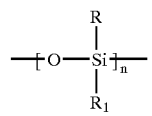

wherein, $n \geq 2$; R1 is at least one of a C1–C4 alkyl, aryl, C1–C4 alkoxy, hydroxy, chloro, or C1–C4 ester group; and wherein R is an amino alkylene or polyamino alkylene group comprising at least one of an N-chloro or an N-bromo group.

53. A chemically modified substrate, comprising the structure

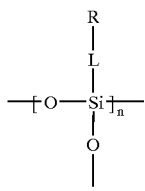

wherein, n≧2; L is a linker group; and wherein R is a heterocyclic N-halamine.

54. A chemically modified substrate, comprising the structure

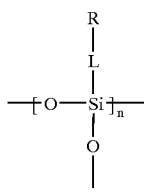

wherein, n≧2; L is a linker group; and wherein R is a heterocyclic amine having the structure

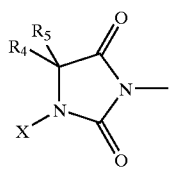

wherein R4 and R5 are independently selected from a C1–C4 alkyl, aryl, or hydroxymethyl group; and wherein X is at least one of chlorine or bromine.

55. A chemically modified substrate, comprising the structure

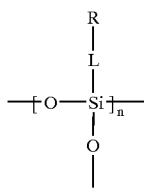

wherein, n≧2; L is a linker group; and wherein R is a heterocyclic N-halamine from at least one of a hydantoin, imidazolidinone, oxazolidinone, isocyanurate, glycoluril, triazinedione, and piperidine.

56. A chemically modified substrate, comprising the structure

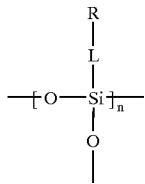

wherein, n≧2; L is a linker group; and wherein R is a heterocyclic amine having the structure

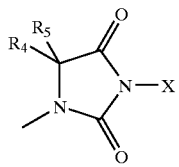

wherein R4 and R5 are independently selected from a C1–C4 alkyl, aryl, or hydroxymethyl group; and wherein X is at least one of chlorine or bromine.

57. A chemically modified substrate, comprising the structure

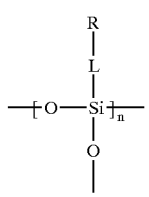

wherein, n≧2; L is a linker group; and wherein R is a heterocyclic amine having the structure

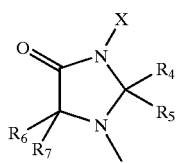

wherein R4, R5, R6, and R7 are independently selected from a C1–C4 alkyl, aryl, or hydroxymethyl group; and wherein X is at least one of chlorine or bromine 58. A chemically modified substrate, comprising the structure

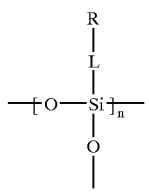

wherein, n≧2; L is a linker group; and wherein R is a heterocyclic amine having the structure

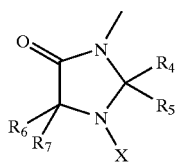

wherein R4, R5, R6, and R7 are independently selected from a C1–C4 alkyl, aryl, or hydroxymethyl group; and wherein X is at least one of chlorine or bromine 59. A chemically modified substrate, comprising the structure

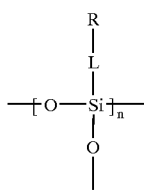

wherein, n≧2; L is a linker group; and wherein R is a heterocyclic amine having the structure

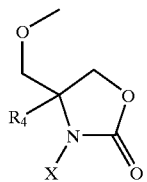

wherein R4 is at least one of a C1–C4 alkyl, aryl, or hydroxymethyl group; and wherein X is at least one of chlorine or bromine 60. A chemically modified substrate, comprising the structure

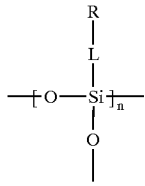

wherein, n≧2; L is a linker group; and wherein R is a heterocyclic amine having the structure

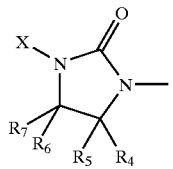

wherein R4, R5, R6, and R7 are independently selected from a C1–C4 alkyl, aryl, or hydroxymethyl group; and wherein X is at least one of chlorine or bromine 61. A chemically modified substrate, comprising the structure

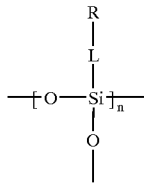

wherein, n≧2; L is a linker group; and wherein R is a heterocyclic amine having the structure

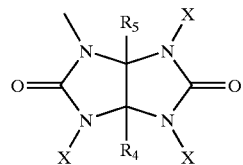

wherein R4 and R5 are independently selected from a C1–C4 alkyl, aryl, or hydroxymethyl group; and wherein X is independently selected from at least one of hydrogen, chlorine, bromine, or hydroxymethyl; and wherein at least one X is chlorine or bromine 62. A chemically modified substrate, comprising the structure

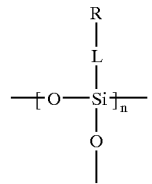

wherein, n≧2; L is a linker group; and wherein R is a heterocyclic amine having either structure

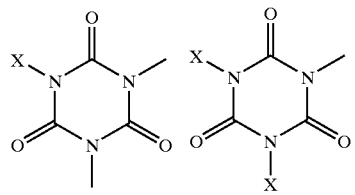

wherein X is independently selected from at least one of hydrogen, chlorine, bromine, or hydroxymethyl; and wherein at least one X is chlorine, or bromine.

63. A chemically modified substrate, comprising the structure

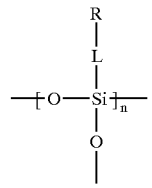

wherein, n≧2; L is a linker group; and wherein R is a heterocyclic amine having the structure

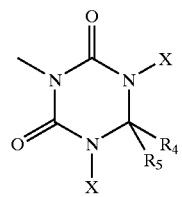

wherein R4 and R5 are independently selected from a C1–C4 alkyl, aryl, or hydroxymethyl group; and wherein X is independently selected from at least one of hydrogen, chlorine, bromine, or hydroxymethyl; and wherein at least one X is chlorine or bromine 64. A chemically modified substrate, comprising the structure

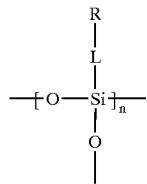

wherein, n≧2; L is a linker group; and wherein R is a heterocyclic amine having the structure

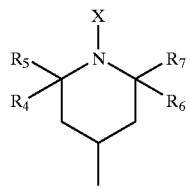

wherein R4, R5, R6, and R7 are independently selected from a C1–C4 alkyl, aryl, or hydroxymethyl group; and wherein X is at least one of chlorine or bromine 65. A chemically modified substrate, comprising the structure

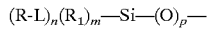

wherein, m=0, 1, or 2; n=1, 2, or 3; p=1, 2, or 3; and m+n+p=4; wherein R is a heterocyclic N-halamine; wherein L is a linker group; and wherein R1 is a C1–C4 alkoxy, hydroxy, chloro, or C1–C4 ester group.

66. A chemically modified substrate, comprising the structure

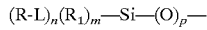

wherein, m=0, 1, or 2; n=1, 2, or 3; p=1, 2, or 3; and n+n+p=4; wherein R is a heterocyclic N-halamine from at least one of a hydantoin, imidazolidinone, oxazolidinone, isocyanurate, glycoluril, triazinedione, and piperidine; L is a linker group; and R1 is a C1–C4 alkoxy, hydroxy, chloro, or C1–C4 ester group.

67. A chemically modified substrate, comprising the structure

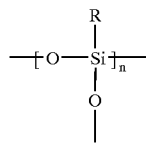

wherein, n≧2; R is an amino alkylene or polyamino alkylene group comprising at least one of an N-chloro or an N-bromo group.

68. A chemically modified substrate, comprising the structure

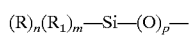

wherein, m=0, 1, or 2; n=1, 2, or 3; p=1, 2, or 3; R1 is independently selected from a C1–C4 alkyl, aryl, C1–C4 alkoxy, hydroxy, chloro, or C1–C4 ester group; and R is an amino alkylene or polyamino alkylene group comprising at least one N-chloro or N-bromo group.

69. A method for making a modified substrate, comprising:
applying a solution of a compound of claim 1, and water, to a substrate;
drying the solution; and
curing the substrate at an elevated temperature to provide a modified substrate.

70. The method of claim 69, wherein the solution further comprises an alcohol.

71. The method of claim 69, wherein the solution is an alkaline solution.

72. A method for making a modified substrate, comprising:
applying a solution of a compound of claim 21, and water, to a substrate;
drying the solution; and
curing the substrate at an elevated temperature to provide a modified substrate.

73. A method for making a modified substrate, comprising:
applying a solution of a silane having a pendant heterocyclic amine, and water, to a substrate;
drying the solution;
curing the substrate at an elevated temperature; and
halogenating the heterocyclic amine with an oxidative halogen compound to provide a modified substrate.

74. A method for making a modified substrate, comprising:
applying a solution of a compound of claim 37, and water, to a substrate;
drying the solution; and
curing the substrate at an elevated temperature to provide a modified substrate.

75. A method for making a modified substrate, comprising:
applying a solution of a silane having a pendant amino alkylene or polyamino alkylene group, and water, to a substrate;
drying the solution;
curing the substrate at an elevated temperature; and
halogenating the amino group with an oxidative halogen compound to provide a modified substrate.

76. A method for making a modified substrate, comprising:
applying a solution of a compound of claim 40, and water, to a substrate;
drying the solution; and
curing the substrate at an elevated temperature to provide a modified substrate.

77. A method for making a modified substrate, comprising:
applying a solution of a siloxane of claim 42, and water, to a substrate;
drying the solution; and
curing the substrate at an elevated temperature to provide a modified substrate.

78. A method for making a modified substrate, comprising:
applying a solution of a siloxane having a pendant heterocyclic amine, and water, to a substrate;

drying the solution;

curing the substrate at an elevated temperature; and halogenating the heterocyclic amine with an oxidative halogen compound to provide a modified substrate.

79. A method for making a modified substrate, comprising:

applying a solution of a siloxane of claim 52, and water, to a substrate;

drying the solution; and curing the substrate at an elevated temperature to provide a modified substrate.

80. A method for making a modified substrate, comprising:

applying a solution of a siloxane having a pendant amino alkylene or polyamino alkylene group, and water, to a substrate;

drying the solution;

curing the substrate at an elevated temperature; and halogenating the amino group with an oxidative halogen compound to provide a modified substrate.

81. A chemical moiety, comprising a silicon atom covalently bonded to:

(a) an oxygen or chlorine atom; and (b) a N-halamine-containing group selected from the group consisting of:

(1) an acyclic N-chloro or N-bromo amino group;

(2) an acyclic N-chloro or N-bromo polyamino group;

(3) a N-chloro or N-bromo hydantoin group;

(4) a N-chloro or N-bromo imidazolidinone group;

(5) a N-chloro or N-bromo oxazolidinone group;

(6) a N-chloro or N-bromo glycoluril group;

(7) a N-chloro or N-bromo isocyanurate group;

(8) a N-chloro or N-bromo triazinedione group; and (9) a N-chloro or N-bromo piperidine group.

82. The siloxane of claim 41, wherein R1 is a methoxy, ethoxy, or hydroxy group; and wherein R4 and R5 are independently selected from a methyl, ethyl, hydroxymethyl or phenyl group.

83. The siloxane of claim 82, wherein R1 is a methoxy or ethoxy group; R4 and R5 are a methyl group, and L is a linker alkylene, amine, or ether group, comprised of 1–7 carbons and 0–1 nitrogen or oxygen atoms, or L is a linker alkylene group, comprised of 1–7 carbons and a carbamate, thiocarbamate, or urea functional group.

84. The siloxane of claim 83, wherein R1 is a methoxy group; X is chlorine; and L is a linker alkylene comprised of 3 carbons.

85. The siloxane of claim 83, wherein R1 is a methoxy group; X is bromine; and L is a linker alkylene comprised of 3 carbons.

86. The siloxane of claim 83, wherein R1 is an ethoxy group; X is chlorine; and L is a linker alkylene comprised of 3 carbons.

87. The siloxane of claim 83, wherein R1 is an ethoxy group; X is bromine; and L is a linker alkylene comprised of 3 carbons.

88. The siloxane of claim 83, wherein R1 is a methoxy group; X is chlorine; and L is a linker amine or ether group comprised of 4 carbons, and 1 nitrogen or oxygen atom.

89. The siloxane of claim 83, wherein R1 is a methoxy group; X is bromine; and L is a linker amine or ether group comprised of 4 carbons, and 1 nitrogen or oxygen atom.

90. The siloxane of claim 83, wherein R1 is an ethoxy group; X is chlorine; and L is a linker amine or ether group comprised of 4 carbons, and 1 nitrogen or oxygen atom.

91. The siloxane of claim 83, wherein R1 is an ethoxy group; X is bromine; and L is a linker amine or ether group comprised of 4 carbons, and 1 nitrogen or oxygen atom.

92. The siloxane of claim 83, wherein R1 is a methoxy group; X is chlorine; and L is a linker alkylene group comprised of 4 carbons and a carbamate, thiocarbamate, or urea functional group.

93. The siloxane of claim 83, wherein R1 is a methoxy group; X is bromine; and L is a linker alkylene group comprised of 4 carbons and a carbamate, thiocarbamate, or urea functional group.

94. The siloxane of claim 83, wherein R1 is an ethoxy group; X is chlorine; and L is a linker alkylene group comprised of 4 carbons and a carbamate, thiocarbamate, or urea functional group.

95. The siloxane of claim 83, wherein R1 is an ethoxy group; X is bromine; and L is a linker alkylene group comprised of 4 carbons and a carbamate, thiocarbamate, or urea functional group.

96. The chemically modified substrate of claim 54, wherein R4 and R5 are independently selected from a methyl, ethyl, hydroxymethyl or phenyl group.

97. The chemically modified substrate of claim 96, wherein R4 and R5 are a methyl group, and L is a linker alkylene, amine, or ether group, comprised of 1–7 carbons and 0–1 nitrogen or oxygen atoms, or L is a linker alkylene group, comprised of 1–7 carbons and a carbamate, thiocarbamate, or urea functional group.

98. The chemically modified substrate of claim 97, wherein L is a linker alkylene comprised of 3 carbons.

99. The chemically modified substrate of claim 97, wherein X is bromine; and L is a linker alkylene comprised of 3 carbons.

100. The chemically modified substrate of claim 97, wherein X is chlorine; and L is a linker alkylene comprised of 3 carbons.

101. The chemically modified substrate of claim 97, wherein X is bromine; and L is a linker alkylene comprised of 3 carbons.

102. The chemically modified substrate of claim 97, wherein X is chlorine; and L is a linker amine or ether group comprised of 4 carbons, and 1 nitrogen or oxygen atom.

103. The chemically modified substrate of claim 97, wherein X is bromine; and L is a linker amine or ether group comprised of 4 carbons, and 1 nitrogen or oxygen atom.

104. The chemically modified substrate of claim 97, wherein X is chlorine; and L is a linker amine or ether group comprised of 4 carbons, and 1 nitrogen or oxygen atom.

105. The chemically modified substrate of claim 97, wherein X is bromine; and L is a linker amine or ether group comprised of 4 carbons, and 1 nitrogen or oxygen atom.

106. The chemically modified substrate of claim 97, wherein X is chlorine; and L is a linker alkylene group comprised of 4 carbons and a carbamate, thiocarbamate, or urea functional group.

107. The chemically modified substrate of claim 97, wherein X is bromine; and L is a linker alkylene group comprised of 4 carbons and a carbamate, thiocarbamate, or urea functional group.

108. The chemically modified substrate of claim 97, wherein X is chlorine; and L is a linker alkylene group comprised of 4 carbons and a carbamate, thiocarbamate, or urea functional group.

109. The chemically modified substrate of claim 97, wherein X is bromine; and L is a linker alkylene group comprised of 4 carbons and a carbamate, thiocarbamate, or urea functional group.

110. The siloxane of claim 51, wherein R1 is a methoxy, ethoxy, or hydroxy group; R4, R5, R6, and R7 are a methyl group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbamate, or urea functional group.

111. The chemically modified substrate of claim 64, wherein R4, R5, R6, and R7 are a methyl group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbamate, or urea functional group.

112. The siloxane of claim 44, wherein R1 is a methoxy, ethoxy, or hydroxy group; R4, R5, R6, and R7 are a methyl group; and L is a linker alkylene, amine, or ether group, comprised of 1–4 carbons, and 0–1 nitrogen or oxygen atoms, or L is a linker alkylene group, comprised of 1–4 carbons, and a carbamate, thiocarbamate, or urea functional group.

113. The chemically modified substrate of claim 57, wherein R4, R5, R6, and R7 are a methyl group; and L is a linker alkylene, amine, or ether group, comprised of 1–4 carbons, and 0–1 nitrogen or oxygen atoms, or L is a linker alkylene group, comprised of 1–4 carbons, and a carbamate, thiocarbamate, or urea functional group.

114. The siloxane of claim 45, wherein R1 is a methoxy, ethoxy, or hydroxy group; R4, R5, R6, and R7 are a methyl group; and L is a linker alkylene, amine, or ether group, comprised of 1–4 carbons, and 0–1 nitrogen or oxygen atoms, or L is a linker alkylene group, comprised of 1–4 carbons, and a carbamate, thiocarbamate, or urea functional group.

115. The chemically modified substrate of claim 58, wherein R4, R5, R6, and R7 are a methyl group; and L is a linker alkylene, amine, or ether group, comprised of 1–4 carbons, and 0–1 nitrogen or oxygen atoms, or L is a linker alkylene group, comprised of 1–4 carbons, and a carbamate, thiocarbamate, or urea functional group.

116. The siloxane of claim 46, wherein R1 is a methoxy, ethoxy, or hydroxy group; R4 is a methyl, ethyl, or hydroxymethyl group; and L is a linker alkylene group, comprised of 1–3 carbons, or L is a linker alkylene group, comprised of 1–3 carbons, and a carbamate, thiocarbamate, or urea functional group.

117. The chemically modified substrate of claim 59, wherein R4 is a methyl, ethyl, or hydroxymethyl group; and L is a linker alkylene group, comprised of 1–3 carbons, or L is a linker alkylene group, comprised of 1–3 carbons, and a carbamate, thiocarbamate, or urea functional group.

118. The siloxane of claim 47, wherein R1 is a methoxy, ethoxy or hydroxy group; R4, R5, R6, and R7 are a methyl group; and L is a linker alkylene, amine, or ether group, comprised of 1–4 carbons, and 0–1 nitrogen or oxygen atoms, or L is a linker alkylene group, comprised of 1–4 carbons, and a carbamate, thiocarbamate, or urea functional group.

119. The chemically modified substrate of claim 60, wherein R4, R5, R6, and R7 are a methyl group; and L is a linker alkylene, amine, or ether group, comprised of 1–4 carbons, and 0–1 nitrogen or oxygen atoms, or L is a linker alkylene group, comprised of 1–4 carbons, and a carbamate, thiocarbamate, or urea functional group.

120. The siloxane of claim 48, wherein R1 is a methoxy, ethoxy, or hydroxy group; R4 and R5 are a methyl group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbamate, or urea functional group.

121. The chemically modified substrate of claim 61, wherein R4 and R5 are a methyl group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbamate, or urea functional group.

122. The siloxane of claim 49, wherein R1 is a methoxy, ethoxy, or hydroxy group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbamate, or urea functional group.

123. The chemically modified substrate of claim 61, wherein L is a linker alkylene, amine, or ether group, comprised of 1–4 carbons and 0–1 nitrogen or oxygen atoms, or L is a linker alkylene group, comprised of 1–4 carbons, and a carbamate, thiocarbamate, or urea functional group.

124. The siloxane of claim 50, wherein R1 is a methoxy, ethoxy, or hydroxy group; R4 and R5 are a methyl group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbamate, or urea functional group.

125. The chemically modified substrate of claim 62, wherein R4 and R5 are a methyl group; and L is a linker alkylene, amine, or ether group, comprised of 1–4 carbons and 0–1 nitrogen or oxygen atoms, or L is a linker alkylene group, comprised of 1–4 carbons, and a carbamate, thiocarbamate, or urea functional group.

* * * * *

UNITED STATES PATENT AND TRADEMARK OFFICE
CERTIFICATE OF CORRECTION

PATENT NO. : 6,969,769 B2
APPLICATION NO. : 10/400,165
DATED : November 29, 2005
INVENTOR(S) : S.D. Worley et al.

It is certified that error appears in the above-identified patent and that said Letters Patent is hereby corrected as shown below:

| COLUMN | LINE | ERROR |
|---|---|---|
| 27 (Claim 2, | 23 line 3) | "of L" should read --or L-- |
| 27 (Claim 2, | 24 line 4) | "carbonate, thiocarbanote," should read --carbamate, thiocarbamate,-- |
| 29 (Claim 20, | 19 line 6) | "thiocarbomate," should read --thiocarbamate,-- |
| 31 (Claim 26, | 12 line 12) | after "chlorine" delete "," |
| 31 (Claim 27, | 44 line 12) | after "chlorine" delete "," |
| 31 (Claim 28, | 50 line 6) | "thiocarbomate," should read --thiocarbamate,-- |
| 32 (Claim 29, | 12 line 12) | after "chlorine" delete "," |
| 32 (Claim 31, | 49 line 14) | after "chlorine" delete "," |
| 32 (Claim 32, | 56 line 6) | "thiocarbomate," should read --thiocarbamate,-- |
| 33 (Claim 33, | 18 line 12) | after "chlorine" delete "," |
| 33 (Claim 34, | 24 line 6) | "thiocarbomate," should read --thiocarbamate,-- |
| 33 (Claim 35, | 54 line 14) | after "chlorine" delete "," |

UNITED STATES PATENT AND TRADEMARK OFFICE
CERTIFICATE OF CORRECTION

PATENT NO. : 6,969,769 B2  
APPLICATION NO. : 10/400,165  
DATED : November 29, 2005  
INVENTOR(S) : S.D. Worley et al.

It is certified that error appears in the above-identified patent and that said Letters Patent is hereby corrected as shown below:

| COLUMN | LINE | ERROR |
|---|---|---|
| 33 (Claim 36, | 60 line 6) | "thiocarbomate," should read --thiocarbamate,-- |
| 35 (Claim 42, | 13-14 lines 6-7) | "an hydantoin" should read --a hydantoin-- |

Signed and Sealed this

Eighth Day of August, 2006

JON W. DUDAS  
*Director of the United States Patent and Trademark Office*

UNITED STATES PATENT AND TRADEMARK OFFICE
CERTIFICATE OF CORRECTION

PATENT NO.        : 6,969,769 B2  
APPLICATION NO.   : 10/400165  
DATED             : November 29, 2005  
INVENTOR(S)       : S.D. Worley et al.

Page 1 of 2

It is certified that error appears in the above-identified patent and that said Letters Patent is hereby corrected as shown below:

| COLUMN | LINE | ERROR |
|---|---|---|
| Item (73) Pg. 1, col. 1 | Assignee | "Assignee: Vanson Halosource, Inc., Redmond, WA (US)" should read --Assignees: Auburn University, Auburn, AL (US) and Vanson Halosource, Inc., Redmond, WA (US)-- |
| 27 (Claim 2, | 23 line 3) | "of L" should read --or L-- |
| 27 (Claim 2, | 24 line 4) | "carbonate, thiocarbanote," should read --carbamate, thiocarbamate,-- |
| 29 (Claim 20, | 19 line 6) | "thiocarbomate," should read --thiocarbamate,-- |
| 31 (Claim 26, | 12 line 12) | after "chlorine" delete "," |
| 31 (Claim 27, | 44 line 12) | after "chlorine" delete "," |
| 31 (Claim 28, | 50 line 6) | "thiocarbomate," should read --thiocarbamate,-- |
| 32 (Claim 29, | 12 line 12) | after "chlorine" delete "," |
| 32 (Claim 31, | 49 line 14) | after "chlorine" delete "," |
| 32 (Claim 32, | 56 line 6) | "thiocarbomate," should read --thiocarbamate,-- |
| 33 (Claim 33, | 18 line 12) | after "chlorine" delete "," |
| 33 (Claim 34, | 24 line 6) | "thiocarbomate," should read --thiocarbamate,-- |

UNITED STATES PATENT AND TRADEMARK OFFICE
CERTIFICATE OF CORRECTION

PATENT NO. : 6,969,769 B2
APPLICATION NO. : 10/400165
DATED : November 29, 2005
INVENTOR(S) : S.D. Worley et al.

It is certified that error appears in the above-identified patent and that said Letters Patent is hereby corrected as shown below:

| COLUMN | LINE | ERROR |
|---|---|---|
| 33 (Claim 35, | 54 line 14) | after "chlorine" delete "," |
| 33 (Claim 36, | 60 line 6) | "thiocarbomate," should read --thiocarbamate,-- |
| 35 (Claim 42 | 13-14 lines 6-7) | "an hydantoin" should read --a hydantoin-- |

Signed and Sealed this

Sixteenth Day of January, 2007

JON W. DUDAS
*Director of the United States Patent and Trademark Office*